United States Patent
Carney et al.

(10) Patent No.: US 9,347,034 B1
(45) Date of Patent: May 24, 2016

(54) METHODS FOR PREVENTING LYSIS IN A CULTURE OF HAEMATOCOCCUS PLUVIALIS USING HYDROGEN PEROXIDE

(71) Applicant: HELIAE DEVELOPMENT LLC, Gilbert, AZ (US)

(72) Inventors: Laura Carney, Chandler, AZ (US); Kristine Sorensen, Chandler, AZ (US)

(73) Assignee: Heliae Development LLC, Gilbert, AZ (US)

( * ) Notice: Subject to any disclaimer, the term of this patent is extended or adjusted under 35 U.S.C. 154(b) by 0 days.

(21) Appl. No.: 14/796,729

(22) Filed: Jul. 10, 2015

Related U.S. Application Data

(63) Continuation of application No. 14/667,917, filed on Mar. 25, 2015, now Pat. No. 9,113,607.

(51) Int. Cl.
  *C12N 1/12* (2006.01)
(52) U.S. Cl.
  CPC ........................................ *C12N 1/12* (2013.01)
(58) Field of Classification Search
  CPC .......................................................... C12N 1/12
  USPC ...................................................... 435/257.1
  See application file for complete search history.

(56) References Cited

U.S. PATENT DOCUMENTS

| | | |
|---|---|---|
| 2007/0196383 A1 | 8/2007 | Murakami |
| 2011/0312063 A1 | 12/2011 | Malm |

FOREIGN PATENT DOCUMENTS

| | | |
|---|---|---|
| EP | 1724337 | 11/2006 |
| JP | 09173050 A | 7/1997 |
| WO | 2006138271 A1 | 12/2006 |
| WO | 2013096770 A1 | 6/2013 |
| WO | 2014016612 A1 | 1/2014 |
| WO | 2014074769 A2 | 5/2014 |

OTHER PUBLICATIONS

Chang et al., "Hydrogen Peroxide Production Protects Chlamydomonas Reinhardtii Against Light-Induced Cell Death by Preventing Singlet Oxygen Accumulation through Enhanced Carotenoid Synthesis," Journal of Plant Physiology, 170 (2013) pp. 976-986.

Schreier et al., "Efficacy of formalin, hydrogen peroxide, and sodium chloride on fungal-infected rainbow trout eggs," Aquaculture 140 (1996) pp. 323-331.

*Primary Examiner* — Tekchand Saidha
(74) *Attorney, Agent, or Firm* — Heliae Development LLC; Justin Kniep; Len Smith

(57) ABSTRACT

Methods of treating lysis in cultures of *Haematococcus pluvialis* with hydrogen peroxide are described herein. The method comprises detecting lysis in the culture and then dosing the culture with a concentration of hydrogen peroxide based on the stage of the cells in the culturing process and at a frequency to increase the likelihood of the cells surviving until the process of accumulating carotenoids, such as astaxanthin, is complete.

15 Claims, No Drawings

METHODS FOR PREVENTING LYSIS IN A CULTURE OF HAEMATOCOCCUS PLUVIALIS USING HYDROGEN PEROXIDE

CROSS REFERENCE TO RELATED APPLICATIONS

This application is a continuation of U.S. application Ser. No. 14/667,917, filed Mar. 25, 2015, entitled Methods for Treating a Culture of *Haematococcus pluvialis* for Contamination Using Hydrogen Peroxide, the entire contents of which are hereby incorporated by reference.

BACKGROUND

*Haematococcus* is a microalga that is capable of producing astaxanthin, a high value carotenoid with antioxidant properties. The culturing process from beginning to end is relatively long compared to other common microalgae, such as *Chlorella* or *Nannochloropsis*, and results in a number of challenges to the survival of *Haematococcus* cells due to the nature of *Haematococcus* as a slow growing microalga. Over the course of the culturing process, the *Haematococcus* cells must go through a growth and cell division phase to accumulate biomass before entering a second stage where growth and motility is halted but astaxanthin is accumulated in the cells before harvest. Operating this long multi-stage culturing process as an open culture increases exposure of the cells to the dangers of contamination, a sub-optimal environment, or other conditions which reduce the survival rate of the cells and ultimately the quantity and quality of the astaxanthin harvest.

Developing treatments for increasing the survival rate of *Haematococcus* cultures must take into account the sensitivities of the cells at the different stages, impact on biomass growth, and impact on astaxanthin production, as well as effectiveness of the treatment over the long culturing process. Treatments developed for faster growing microalgae or microalgae cultured for production of whole biomass, lipids, or proteins, such as treatment with oxidative agents or commercially available herbicides, fungicides, and pesticides, have not been shown to be easily translatable to *Haematococcus* cultures due to the unique stages of the *Haematococcus* culturing process, the sensitivities of *Haematococcus* cells, and the desire to use the targeted end product of *Haematococcus* cultures in human consumption product industries (e.g., nutritional supplements, food enhancers, therapeutic compositions). Therefore, there is a need in the art to development treatment methods for increasing the survival rate of *Haematococcus* cells before and during the astaxanthin accumulation stage, without adversely affecting the cells and value of the end product.

SUMMARY

In one non-limiting embodiment of the invention, a method of culturing *Haematococcus pluvialis*, may comprise: culturing a population of *Haematococcus pluvialis* cells in growth conditions in a liquid culture medium to obtain a culture of *Haematococcus pluvialis* cells in which the cells are primarily in the green swimmer stage; contacting the primarily green swimmer stage culture with hydrogen peroxide to form a calculated concentration in the range of 0.005-0.020 mL of hydrogen peroxide per L of culture medium (mL/L); and culturing the *Haematococcus pluvialis* cells in reddening conditions to form cells in the red cyst stage for accumulation of carotenoids.

In some embodiments, the calculated concentration of hydrogen peroxide may be in the range of 0.005-0.010 mL/L. In some embodiments, the calculated concentration of hydrogen peroxide may be in the range of 0.010-0.015 mL/L. In some embodiments, the calculated concentration of hydrogen peroxide is in the range of 0.015-0.020 mL/L.

In some embodiments, the growth conditions may comprise a photosynthetically active radiation intensity in the range of 30-60 mol m$^{-2}$ d$^{-1}$, nitrate concentration in the range of 20-50 ppm in the culture medium, and less than 1 ppt of sodium chloride in the culture medium. In some embodiments, the reddening conditions may comprise the present of 1-5 ppt sodium chloride in the culture medium.

In some embodiments, the method may further comprise determining a level of chytrids in the culture of *Haematococcus pluvialis* cells as a percentage of infected cells out of the total cells in a culture. In some embodiments, the culture of *Haematococcus pluvialis* cells may be contacted with the hydrogen peroxide when the level of chytrids is less than 20%. In some embodiments, the culture of *Haematococcus pluvialis* cells is contacted with the hydrogen peroxide when the level of chytrids is at least 5%.

In some embodiments, the level of chytrids in the culture may be maintained below the level of chytrids at the time of contact with hydrogen peroxide while culturing the *Haematococcus pluvialis* cells in reddening conditions to produce cells in the red cyst stage for the accumulation of carotenoids. In some embodiments, the chytrid level after contacting the culture with hydrogen peroxide may be 20-95% less than a control culture not receiving treatment with hydrogen peroxide.

In some embodiments, the cells may be contacted with the hydrogen peroxide multiple times. In some embodiments, the cells may be contacted with the hydrogen peroxide every 6-24 hours. In some embodiments, the cells may be contacted with the hydrogen peroxide every 6-12 hours. In some embodiments, the cells may be contacted with the hydrogen peroxide every day over the course of 1-14 days. In some embodiments, the cells may be contacted with hydrogen peroxide every other day over the course of 3-15 days.

In some embodiments, the biomass yield of the *Haematococcus pluvialis* cells contacted with the hydrogen peroxide may be equivalent to or greater than a control culture not receiving treatment with hydrogen peroxide. In some embodiments, the biomass yield of the *Haematococcus pluvialis* cells contacted with the hydrogen peroxide may be 0.01-0.25 g/L greater than a control culture not receiving treatment with hydrogen peroxide.

In some embodiments, the carotenoids yield of the *Haematococcus pluvialis* cells contacted with the hydrogen peroxide may be equivalent to or greater than a control culture not receiving treatment with hydrogen peroxide. In some embodiments, the carotenoid yield of the *Haematococcus pluvialis* cells contacted with the hydrogen peroxide may be 0.10-1.50% greater than a control culture not receiving treatment with hydrogen peroxide.

DETAILED DESCRIPTION OF THE INVENTION

Overview

*Haematococcus* is a genus of microalgae classified in the Eukaryota domain, Viridiplantae kingdom, Chlorophyta phylum, Chlorophyceae class, Chlamydomonadales order, and Haematococcaceae family. The species *Haematococcus pluvialis* is typically grown in phototrophic conditions and is of particular interest commercially for the production of astaxanthin, a high value carotenoid (i.e., organic pigment) with strong antioxidant properties. While *Haematococcus pluvialis* produces astaxanthin, the level of astaxanthin in the cell is dependent on the culturing conditions and is not present at a constant level in the cell over the life of the cell.

*Haematococcus pluvialis* has been studied academically and produced commercially, and thus conventional culture conditions may be found in literature in the public domain. A culture of *Haematococcus pluvialis* cells begins in growth conditions, where the cells are primarily (i.e., at least 80% of cells) in the green swimmer stage in which the cells may grow and divide but have low levels of astaxanthin. The term "green swimmer" refers to a state of the *Haematococcus pluvialis* cell in which the cell is in a motile state, contains cilia, and has a larger proportion of chlorophyll (i.e., green pigment) than carotenoids (i.e., red pigment from astaxanthin). *Haematococcus pluvialis* cells may also exist in a non-motile or cyst stage when the cell has a larger proportion of chlorophyll (i.e., green pigment) than carotenoids (i.e., red pigment from astaxanthin), which may be referred to as a "green cyst". The term "growth conditions" refers to culture conditions that facilitate the growth and cell division of the *Haematococcus pluvialis* cells, and minimize the stressors that may cause a cell to enter a resting state. Growth conditions for *Haematococcus pluvialis* cells may comprise light in the photosynthetically active radiation (PAR) wavelengths, carbon dioxide, and a liquid medium comprising primarily water, nitrogen, phosphorus and trace metal nutrients.

As *Haematococcus pluvialis* cells mature, they transition to a red cyst stage where cell division halts or slows but astaxanthin is accumulated as the cell is stressed by reddening conditions. The term "red cyst" refers to a state of the *Haematococcus pluvialis* cell in which the cell is in a resting state, has lost the cilia, and has a larger proportion of carotenoids (i.e., red pigment from astaxanthin) than chlorophyll (i.e., green pigment). The term "reddening conditions" refers to culture conditions that stress the *Haematococcus pluvialis* cells to facilitate the transition to a resting state and accumulation of carotenoids (e.g., astaxanthin) in the cells. Reddening conditions for *Haematococcus pluvialis* may comprise nitrogen or other nutrient deprivation, addition of bi-carbonate, addition of bleach, and increased levels of salinity, light intensity, and/or temperature as compared to growth conditions.

Due to the size of *Haematococcus* cells, the culture is actively mixed by means known in the art such as, but not limited to, paddlewheels, gas sparging, and mechanical stirrers, in order to prevent the cells from settling to the bottom of the bioreactor and to circulate the cells for exposure to available light and nutrients. *Haematococcus pluvialis* may be cultured in a number of systems known in the art that meet the shear sensitivity requirements for green swimmer cells such as, but not limited to, column bioreactors with gas sparger mixing, raceway pond bioreactors with paddlewheel mixing, and bag bioreactors with gas sparger mixing.

The process of culturing a small volume *Haematococcus* culture through the green swimmer stage to a large volume in the red cyst stage may take weeks due to the slow rate at which *Haematococcus* grows, divides, and accumulates carotenoids. During this time period the *Haematococcus* cells are vulnerable to weakening of the physical integrity of the cells (e.g., lysis) and to attacks by contamination (e.g., bacteria, fungi, predator organisms, other microalgae) which reduce the chances of *Haematococcus* survival in both the green swimmer and red cyst stages. The term "lysis" refers to *Haematococcus pluvialis* cells losing the integrity of the cell membrane and breaking open the outside of the halo or lysing the internal cytoplasm without halo breakage, and is expressed as a % of the total *Haematococcus pluvialis* cells in the culture.

For example, the occurrence of lysis in the green swimmer stage and a chytrid infection in the non-motile cell stages, including green and red cyst stage, have been observed to rapidly kill the majority of *Haematococcus* cells in a culture. Chytrids are a basal fungus which operates by attaching to microalgae cells, growing into the microalgae cell, reproducing in the cell, and subsequently attacking more microalgae cells. Such a loss of a *Haematococcus* culture after resources have been expended to culture the cells for multiple days or weeks, but before a harvest of the cells with a desirable level of astaxanthin can be obtained, may be devastating for a commercial operation. The vulnerability of the *Haematococcus* cells is further amplified in open cultures (e.g., open pond bioreactors), where conditions are harder to control and contamination is more easily introduced.

The length of the culturing process for *Haematococcus* increases the necessity for treatments to the culture be capable of application multiple times over the course of the culturing process without harming the *Haematococcus* cells, or application of a high initial concentration that remains effective for a long period but does not harm the *Haematococcus* cells at the initial application. Treatments where the *Haematococcus* could not tolerate a one-time application at an initial concentration high enough to maintain effectiveness against contamination over time, or where multiple applications would accumulate a concentration level toxic to the *Haematococcus* would not achieve the goal of getting the culture to a successful harvest. Additionally, the sensitivity of the *Haematococcus* cells is dependent on the stage or state of the cells, with the green swimmer cells being more sensitive than the red cyst cells. For example, lysis is more likely to occur within a culture of green swimmer cells than in a culture of red cyst cells, and green swimmer cells are less tolerant of salt than red cyst cells. A general treatment may only be effective for one stage of a *Haematococcus* culture or may be harmful to cells in a certain state, therefore a successful treatment over the life of a *Haematococcus* culture must take into account the state of the cells in order to maximize effectiveness and minimize or eliminate adverse effects on the cells.

Tests of available treatments, including chemical biocides, blends of natural organic herbs, bleach, sodium hydroxide, and biological agents were found to have varying levels of effectiveness against chytrids in examples 13-17. However, the public domain knowledge for these available treatments does not address how these treatments will affect *Haematococcus* cells in the green swimmer and red cyst stages, and therefore do not provide immediately available solutions to the described challenges faced in culturing *Haematococcus*.

Known methods of adaptation or genetic modification may be used to alter the *Haematococcus* cells for increased resistance to lysis or contamination, however the process may be long and expensive. Additionally, genetic modification may limit product markets available for using the *Haematococcus* derived astaxanthin.

The inventors have developed the described methods specific to the green swimmer and cyst stages, including red cysts and green cysts, for use in the contexts of prevention of lysis or fungal infection of a *Haematococcus* culture and treating a culture of *Haematococcus* cells with existing levels of lysis or fungal infection. Some embodiments of the methods may be used multiple times to treat the same culture of *Haematococcus*, including treating the same culture multiple times in a single day, while minimizing or eliminating any negative effect on the biomass yield and carotenoid yield of the cells.

The inventors surprisingly found that treatment of a culture of *Haematococcus pluvialis* with hydrogen peroxide was successful in preventing and treating lysis in a culture of *Haematococcus* cells without negatively effecting biomass accumulation and productivity of the cells, even when administered multiple times. The inventors also surprisingly found that treatments of a culture of *Haematococcus pluvialis* with hydrogen peroxide, salt, or hydrogen peroxide in combination with salt were successful in preventing and treating a chytrid infection in a culture of *Haematococcus* cells without negatively affecting biomass accumulation, productivity, and carotenoid accumulation, even when administered multiple times. Hydrogen peroxide was also found to be advantageous due to the ability to dissipate quickly in the *Haematococcus* culture (e.g., degrades to undetectable levels within 2 hours of application), which allows multiple applications to be applied without the danger of buildup of residual concentrations or detection in the final harvested product. Salt was treatments were found to be advantageous in that the concentration of salt in the culture may be a result of an single dosing at a desired concentration or multiple doses building up to the desired concentration, but remain effective over time without determinant to the *Haematococcus* cells or harvested product.

Hydrogen peroxide may be purchased commercially at different stock concentrations, therefore a calculated concentration was used to describe the inventive methods. The term "calculated concentration" is a concentration value for a contamination treatment solution calculated by multiplying the volume of the treatment solution per culture volume (e.g., mL of hydrogen peroxide/L of microalgae culture medium) by the percent stock concentration of the contamination treatment solution. The calculated concentration expressed is in units of volume/volume (e.g., mL/L) for a theoretical 100% stock concentration of treatment solution applied to a microalgae culture. For example, a 1 L microalgae culture treated with 10 mL of a hydrogen peroxide solution of a stock concentration of 50% would have a calculated concentration=10 mL/L×0.5=5 mL/L contamination treatment solution.

The described methods of applying an effective concentration of hydrogen peroxide, salt, or combination of hydrogen peroxide and salt to a culture of *Haematococcus* may prevent the occurrence of lysis or a chytrid infection, prevent an increase in the lysis or chytrid infection level (i.e., maintain the level), slow the increase of the lysis or chytrid infection level, or decrease the lysis or chytrid infection level in order to increase the survival rate of the *Haematococcus* cells and decrease any negative effect on the accumulation of astaxanthin. The level of tolerance a culture of *Haematococcus* has for lysis or chytrids may vary depending on the strain, culture conditions, and bioreactor system. Some cultures may be able to survive a lysis or chytrid infection level above 50%, while other cultures may only survive at lower levels such as below 30%, 20%, 10%, or 5%.

While the prior art has generally disclosed the presence of hydrogen peroxide in a microalgae or cyanobacteria culture for a variety of functions, the teachings of the prior art relate to the use of hydrogen peroxide in contexts not directly translatable to culturing *Haematococcus* for astaxanthin product, such as: sterilizing bioreactors with vapor hydrogen peroxide and culturing cyanobacteria genetically modified for resistance to the residual hydrogen peroxide (0.0024-1.1790 mL/L) from the bioreactor sterilization step; killing bacteria in a microalgae culture with intermittent doses of hydrogen peroxide (0.00001-0.2 mL/L, 0.0590-0.7074 mL/L); and providing lethal stress conditions for programmed death of a genetically modified microalgae using hydrogen peroxide (at least 0.1769 mL/L). The wide ranges of hydrogen peroxide for different purposes disclosed in the prior art do not address effective concentrations that treat or prevent lysis and fungal infections while avoiding adverse effects on *Haematococcus* in green swimmer and red cyst cell stages. Due to this deficiency in the publically available information, such determinations for the proper concentrations of hydrogen peroxide and methods of application for *Haematococcus* cells in various stages of the culturing process were determined through extensive experimentation of two different *Haematococcus pluvialis* strains by the inventors. Additionally, the extensive experimentation by the inventors resulted in the methods of effectively promoting survival of *Haematococcus* cells through prevention and treatment of lysis and fungal infections while also not adversely affecting biomass accumulation, productivity, and carotenoid accumulation of the cells, which is an additional step of commercial importance not addressed by the prior art.

Method Embodiments

In one non-limiting embodiment, a method of preventing and/or treating a chytrid infection in a culture of *Haematococcus* may comprise: culturing a population of *Haematococcus* cells in growth conditions in a liquid culture medium to obtain a culture of *Haematococcus* cells in which the cells are primarily (i.e., at least 80%) in the green swimmer stage; contacting the primarily green swimmer cell stage culture with an effective amount of hydrogen peroxide; and culturing the *Haematococcus* cells in reddening conditions to form cells in the red cyst stage for the accumulation of carotenoids, such as astaxanthin.

In some embodiments, the *Haematococcus* cells may be contacted with hydrogen peroxide to form a calculated concentration in the range of 0.005-0.025 mL/L. In some embodiments, the *Haematococcus* cells may be contacted with hydrogen peroxide to form a calculated concentration in the range of 0.005-0.020 mL/L. In some embodiments, the *Haematococcus* cells may be contacted with hydrogen peroxide to form a calculated concentration in the range of 0.005-0.010 mL/L. In some embodiments, the *Haematococcus* cells may be contacted with hydrogen peroxide to form a calculated concentration in the range of 0.010-0.015 mL/L. In some embodiments, the *Haematococcus* cells may be contacted with hydrogen peroxide to form a calculated concentration in the range of 0.015-0.020 mL/L. In some embodiments, the *Haematococcus* cells may be contacted with hydrogen peroxide to form a calculated concentration in the range of 0.020-0.025 mL/L.

The hydrogen peroxide may be in liquid form. In some embodiments, the hydrogen peroxide may be introduced into the culture at a location of active mixing such as, but not limited to at the point of paddlewheel or mechanical stifling, and a point of high turbulence caused by gas sparging. In some embodiments, the hydrogen peroxide may be added all at a single point. In some embodiments, the hydrogen peroxide may be evenly applied over a surface area.

In some embodiments, the cells may be contacted with hydrogen peroxide multiple times. In some embodiments, the cells may be contacted with hydrogen peroxide multiple times while the cells are in the green swimmer stage. In some embodiments, the cells may be contacted with hydrogen peroxide multiple times while the cells are in the red cyst stage. In some embodiments, the cells may be contacted with hydrogen peroxide multiple times while the cell stages span the green swimmer and red cyst stage. In some embodiments, the cells may be contacted multiple times while the culture is in growth conditions. In some embodiments, the cells may be contacted multiple times while the culture is in reddening conditions. In some embodiments, the cells may be contacted multiple times while the culture conditions span growth and reddening conditions.

In some embodiments, the cells may be contacted with hydrogen peroxide 2-4 times per day. In some embodiments, the cells may be contacted with hydrogen peroxide every 6-24 hours. In some embodiments, the cells may be contacted with hydrogen peroxide every 6-8 hours. In some embodiments, the cells may be contacted with hydrogen peroxide every 6-12 hours. In some embodiments, the cells may be contacted with hydrogen peroxide every 12-18 hours. In some embodiments, the cells may be contacted with hydrogen peroxide every 18-24 hours.

In some embodiments, the cells may be contacted with hydrogen peroxide every day over the course of 1-14 days. In some embodiments, the cells may be contacted with hydrogen peroxide every day over the course of 1-2 days. In some embodiments, the cells may be contacted with hydrogen peroxide every day over the course of 1-3 days. In some embodiments, the cells may be contacted with hydrogen peroxide every day over the course of 1-5 days. In some embodiments, the cells may be contacted with hydrogen peroxide every day over the course of 5-7 days. In some embodiments, the cells may be contacted with hydrogen peroxide every day over the course of 7-10 days. In some embodiments, the cells may be contacted with hydrogen peroxide every day over the course of 10-12 days. In some embodiments, the cells may be contacted with hydrogen peroxide every day over the course of 12-14 days.

In some embodiments, the cells may be contacted with hydrogen peroxide every 24-72 hours. In some embodiments, the cells may be contacted with hydrogen peroxide every 36-60 hours. In some embodiments, the cells may be contacted with hydrogen peroxide every 42-54 hours. In some embodiments, the cells may be contacted with hydrogen peroxide every other day over the course of 3-15 days. In some embodiments, the cells may be contacted with hydrogen peroxide every other day over the course of 3-5 days. In some embodiments, the cells may be contacted with hydrogen peroxide every other day over the course of 5-7 days. In some embodiments, the cells may be contacted with hydrogen peroxide every other day over the course of 7-9 days. In some embodiments, the cells may be contacted with hydrogen peroxide every other day over the course of 9-11 days. In some embodiments, the cells may be contacted with hydrogen peroxide every other day over the course of 11-13 days. In some embodiments, the cells may be contacted with hydrogen peroxide every other day over the course of 13-15 days.

In some embodiments, the cells may contacted with hydrogen peroxide in a combination of days over an extended time period, such as every day for a period of days and then every other day for a period of days, or vis versa. For example, the cells may be contacted with hydrogen peroxide every day for a period of 1-5 days and then every other day for a period of 3-15 days. In other embodiments, the cells may contacted with hydrogen peroxide with more than one day in between applications, such as but not limited to, 2 days, 3 days, 4 days, 5 days, 6 days, 7 days, or more between applications. In some embodiments, an application of hydrogen peroxide at a scheduled time (e.g., after 6 hours, after 24 hours) may be skipped and application may be resumed at a later time.

In some embodiments, the growth conditions for a culture of *Haematococcus* may comprise a photosynthetically active radiation (PAR) intensity in the range of 30-60 mol m$^{-2}$ d$^{-1}$. In some embodiments, the growth conditions for a culture of *Haematococcus* may comprise a nitrate concentration in the range of 20-50 ppm. In some embodiments, the growth conditions for a culture of *Haematococcus* may comprise a concentration of less than 1 ppt salt, such as sodium chloride, in the culture medium.

In some embodiments, the reddening conditions for a culture of *Haematococcus* may comprise the presence of salt in the culture medium. In some embodiments, the concentration of sodium chloride in the reddening conditions may comprise 1-5 ppt. In some embodiments, the concentration of sodium chloride in the reddening conditions may comprise 1-2 ppt. In some embodiments, the concentration of sodium chloride in the reddening conditions may comprise 1-3 ppt. The salt may comprise but is not limited to sodium chloride.

In some embodiments, a level of chytrids or chytrid infection in a culture of *Haematococcus* may be determined and expressed as a percentage of infected cells out of the total cells in a culture. In some embodiments, the culture of *Haematococcus* cells may be contacted with hydrogen peroxide when the level of chytrids is less than 60%. In some embodiments, the culture of *Haematococcus* cells may be contacted with hydrogen peroxide when the level of chytrids is less than 50%. In some embodiments, the culture of *Haematococcus* cells may be contacted with hydrogen peroxide when the level of chytrids is less than 40%. In some embodiments, the culture of *Haematococcus* cells may be contacted with hydrogen peroxide when the level of chytrids is less than 30%. In some embodiments, the culture of *Haematococcus* cells may be contacted with hydrogen peroxide when the level of chytrids is less than 20%. In some embodiments, the culture of *Haematococcus* cells may be contacted with hydrogen peroxide when the level of chytrids is less than 10%. In some embodiments, the culture of *Haematococcus* cells may be contacted with hydrogen peroxide when the level of chytrids is less than 5%. In some embodiments, the culture of *Haematococcus* cells may be contacted with hydrogen peroxide when the level of chytrids is less than 3%. In some embodiments, the culture of *Haematococcus* cells may be contacted with hydrogen peroxide when the level of chytrids is less than 2%. In some embodiments, the culture of *Haematococcus* cells may be contacted with hydrogen peroxide when the level of chytrids is less than 1%. In some embodiments, the culture of *Haematococcus* cells may be contacted with hydrogen peroxide when the level of chytrids is 0%.

In some embodiments, the culture of *Haematococcus* cells may be contacted with hydrogen peroxide when the level of chytrids is at least 1%. In some embodiments, the culture of *Haematococcus* cells may be contacted with hydrogen peroxide when the level of chytrids is at least 2%. In some embodiments, the culture of *Haematococcus* cells may be contacted with hydrogen peroxide when the level of chytrids is at least 5%. In some embodiments, the culture of *Haematococcus* cells may be contacted with hydrogen peroxide when the level of chytrids is at least 10%. In some embodiments, the culture of *Haematococcus* cells may be contacted with hydrogen peroxide when the level of chytrids is at least 20%. In some embodiments, the culture of *Haematococcus* cells may be contacted with hydrogen peroxide when the level of chytrids is at least 30%. In some embodiments, the culture of *Haematococcus* cells may be contacted with hydrogen peroxide when the level of chytrids is at least 40%. In some embodiments, the culture of *Haematococcus* cells may be contacted with hydrogen peroxide when the level of chytrids is at least 50%. In some embodiments, the level of chytrids in a culture of *Haematococcus* cells may be maintained below the level of chytrids at the time of contact with hydrogen peroxide while culturing the *Haematococcus* cells in reddening conditions to form cells in the red cyst stage for the accumulation of carotenoids.

In some embodiments, the chytrid level after contacting the culture with hydrogen peroxide may be less than a control culture not receiving treatment with hydrogen peroxide. In some embodiments, the chytrid level after contacting the culture with hydrogen peroxide may be reduced by 20-95% compared to a control culture not receiving treatment with hydrogen peroxide. In some embodiments, the chytrid level after contacting the culture with hydrogen peroxide may be reduced by 20-30% compared to a control culture not receiving treatment with hydrogen peroxide. In some embodiments, the chytrid level after contacting the culture with hydrogen peroxide may be reduced by 30-40% compared to a control culture not receiving treatment with hydrogen peroxide. In some embodiments, the chytrid level after contacting the culture with hydrogen peroxide may be reduced by 40-50% compared to a control culture not receiving treatment with hydrogen peroxide. In some embodiments, the chytrid level after contacting the culture with hydrogen peroxide may be reduced by 50-60% compared to a control culture not receiving treatment with hydrogen peroxide. In some embodiments, the chytrid level after contacting the culture with hydrogen peroxide may be reduced by 60-70% compared to a control culture not receiving treatment with hydrogen peroxide. In some embodiments, the chytrid level after contacting the culture with hydrogen peroxide may be reduced by 70-80% compared to a control culture not receiving treatment with hydrogen peroxide. In some embodiments, the chytrid level after contacting the culture with hydrogen peroxide may be reduced by 80-90% compared to a control culture not receiving treatment with hydrogen peroxide. In some embodiments, the chytrid level after contacting the culture with hydrogen peroxide may be reduced by 90-95% compared to a control culture not receiving treatment with hydrogen peroxide.

In some embodiments, the chytrid level after contacting the culture with hydrogen peroxide in combination with salt may be less than a control culture not receiving treatment. In some embodiments, the chytrid level after contacting the culture with hydrogen peroxide in combination with salt may be reduced by 10-95% compared to a control culture not receiving treatment. In some embodiments, the chytrid level after contacting the culture with hydrogen peroxide in combination with salt may be reduced by 10-30% compared to a control culture not receiving treatment. In some embodiments, the chytrid level after contacting the culture with hydrogen peroxide in combination with salt may be reduced by 30-60% compared to a control culture not receiving treatment. In some embodiments, the chytrid level after contacting the culture with hydrogen peroxide in combination with salt may be reduced by 60-95% compared to a control culture not receiving treatment.

In some embodiments, the biomass yield of the *Haematococcus* cells contacted with hydrogen peroxide is equivalent to or greater than a control culture not receiving treatment with hydrogen peroxide. In some embodiments, the biomass yield of the *Haematococcus* cells contacted with hydrogen peroxide is 0.01-0.25 g/L greater than a control culture not receiving treatment with hydrogen peroxide. In some embodiments, the biomass yield of the *Haematococcus* cells contacted with hydrogen peroxide is 0.01-0.05 g/L greater than a control culture not receiving treatment with hydrogen peroxide. In some embodiments, the biomass yield of the *Haematococcus* cells contacted with hydrogen peroxide is 0.05-0.10 g/L greater than a control culture not receiving treatment with hydrogen peroxide. In some embodiments, the biomass yield of the *Haematococcus* cells contacted with hydrogen peroxide is 0.10-0.15 g/L greater than a control culture not receiving treatment with hydrogen peroxide. In some embodiments, the biomass yield of the *Haematococcus* cells contacted with hydrogen peroxide is 0.15-0.20 g/L greater than a control culture not receiving treatment with hydrogen peroxide. In some embodiments, the biomass yield of the *Haematococcus* cells contacted with hydrogen peroxide is 0.20-0.25 g/L greater than a control culture not receiving treatment with hydrogen peroxide.

In some embodiments, the biomass yield of the *Haematococcus* cells contacted with hydrogen peroxide in combination with salt is equivalent to or greater than a control culture not receiving treatment. In some embodiments, the biomass yield of the *Haematococcus* cells contacted with hydrogen peroxide in combination with salt is 0.01-0.30 g/L greater than a control culture not receiving treatment. In some embodiments, the biomass yield of the *Haematococcus* cells contacted with hydrogen peroxide in combination with salt is 0.01-0.10 g/L greater than a control culture not receiving treatment. In some embodiments, the biomass yield of the *Haematococcus* cells contacted with hydrogen peroxide in combination with salt is 0.10-0.20 g/L greater than a control culture not receiving treatment. In some embodiments, the biomass yield of the *Haematococcus* cells contacted with hydrogen peroxide in combination with salt is 0.20-0.30 g/L greater than a control culture not receiving treatment.

In some embodiments, the carotenoid yield of the *Haematococcus* cells contacted with hydrogen peroxide is equivalent to or greater than a control culture not receiving treatment with hydrogen peroxide. In some embodiments, the carotenoid yield of the *Haematococcus* cells contacted with hydrogen peroxide is 0.10-1.50% greater than a control culture not receiving treatment with hydrogen peroxide. In some embodiments, the carotenoid yield of the *Haematococcus* cells contacted with hydrogen peroxide is 0.10-0.25% greater than a control culture not receiving treatment with hydrogen peroxide. In some embodiments, the carotenoid yield of the *Haematococcus* cells contacted with hydrogen peroxide is 0.25-0.50% greater than a control culture not receiving treatment with hydrogen peroxide. In some embodiments, the carotenoid yield of the *Haematococcus* cells contacted with hydrogen peroxide is 0.50-0.75% greater than a control culture not receiving treatment with hydrogen peroxide. In some embodiments, the carotenoid yield of the *Haematococcus* cells contacted with hydrogen peroxide is 0.75-1.00% greater than a control culture not receiving treatment with hydrogen peroxide. In some embodiments, the carotenoid yield of the *Haematococcus* cells contacted with hydrogen peroxide is 1.00-1.25% greater than a control culture not receiving treatment with hydrogen peroxide. In some embodiments, the carotenoid yield of the *Haematococcus* cells contacted with hydrogen peroxide is 1.25-1.50% greater than a control culture not receiving treatment with hydrogen peroxide.

In some embodiments, the method may further comprise transferring the culture of *Haematococcus* cells to a new culturing vessel after contacting the culture with the hydrogen peroxide. In some embodiments, the culture may be contacted with hydrogen peroxide when the culture is at an optimal temperature. In some embodiments, the culture may be contacted with hydrogen peroxide when the culture is at an optimal culture density.

In another non-limiting embodiment, a method of preventing and/or treating a chytrid infection in a culture of *Haematococcus* may comprise: culturing a population of *Haematococcus* cells in reddening conditions in a liquid culture medium comprising 1-5 ppt of salt to obtain a culture of *Haematococcus* cells in which the cells are primarily (i.e., at least 80%) in the red cyst stage for the accumulation of carotenoids, such as astaxanthin; and contacting the primarily red cyst cell stage culture with an effective amount of hydrogen peroxide. In some embodiments, the *Haematococcus* cells in which the cells may be primarily (i.e., at least 80%) in the green cyst stage in reddening conditions, a combination of green and red cysts in reddening conditions, or a non-motile state in reddening conditions when contacted with an effective amount of hydrogen peroxide.

In another non-limiting embodiment, a method of treating a chytrid infection in a culture of *Haematococcus* may comprise: culturing a population of *Haematococcus* cells in reddening conditions in a liquid culture medium to obtain a culture of *Haematococcus* cells in which the cells are primarily (i.e., at least 80%) in the red cyst stage for the accumulation of carotenoids, such as astaxanthin; detecting a presence of chytrids in the culture; and contacting the culture comprising chytrids and primarily red cyst cells with an effective amount of salt. In some embodiments, the *Haematococcus* cells in which the cells may be primarily (i.e., at least 80%) in the green cyst stage in reddening conditions, a combination of green and red cysts in reddening conditions, or a non-motile state in reddening conditions when contacted with an effective amount of salt.

In some embodiments, the salt contacting the chytrids and red cyst cells may be sodium chloride. In some embodiments, the effective amount of sodium chloride is at least 1.5 times the amount of sodium chloride found in typical reddening conditions, and may be up to 10 times. In some embodiments, the concentration of sodium chloride contacting the chytrids and red cyst cells may be 1-20 ppt. In some embodiments, the concentration of sodium chloride contacting the chytrids and red cyst cells may be 1-2 ppt. In some embodiments, the concentration of sodium chloride contacting the chytrids and red cyst cells may be 1-3 ppt. In some embodiments, the concentration of sodium chloride contacting the chytrids and red cyst cells may be 1-5 ppt. In some embodiments, the concentration of sodium chloride contacting the chytrids and red cyst cells may be 5-10 ppt. In some embodiments, the concentration of sodium chloride contacting the chytrids and red cyst cells may be 10-15 ppt. In some embodiments, the concentration of sodium chloride contacting the chytrids and red cyst cells may be 15-20 ppt.

In some embodiments, the culture of *Haematococcus* cells may be contacted with salt when a level of cells infected by chytrids is less than 60%. In some embodiments, the culture of *Haematococcus* cells may be contacted with salt when a level of cells infected by chytrids is less than 50%. In some embodiments, the culture of *Haematococcus* cells may be contacted with salt when a level of cells infected by chytrids is less than 40%. In some embodiments, the culture of *Haematococcus* cells may be contacted with salt when a level of cells infected by chytrids is less than 30%. In some embodiments, the culture of *Haematococcus* cells may be contacted with salt when a level of cells infected by chytrids is less than 20%. In some embodiments, the culture of *Haematococcus* cells may be contacted with salt when a level of cells infected by chytrids is less than 10%. In some embodiments, the culture of *Haematococcus* cells may be contacted with salt when a level of cells infected by chytrids is less than 5%. In some embodiments, the culture of *Haematococcus* cells may be contacted with salt when a level of cells infected by chytrids is less than 4%. In some embodiments, the culture of *Haematococcus* cells may be contacted with salt when a level of cells infected by chytrids is less than 3%. In some embodiments, the culture of *Haematococcus* cells may be contacted with salt when a level of cells infected by chytrids is less than 2%. In some embodiments, the culture of *Haematococcus* cells may be contacted with salt when a level of cells infected by chytrids is less than 1%. In some embodiments, the culture of *Haematococcus* cells may be contacted with salt when a level of cells infected by chytrids is 0%. In some embodiments, the level of chytrids in the culture may be maintained below the level of chytrids at the time of contact with the salt while culturing the *Haematococcus* cells in reddening conditions to form cells in the red cyst stage for the accumulation of carotenoids.

In some embodiments, the culture of *Haematococcus* cells may be contacted with salt when a level of cells infected by chytrids is at least 1%. In some embodiments, the culture of *Haematococcus* cells may be contacted with salt when a level of cells infected by chytrids is at least 2%. In some embodiments, the culture of *Haematococcus* cells may be contacted with salt when a level of cells infected by chytrids is at least 5%. In some embodiments, the culture of *Haematococcus* cells may be contacted with salt when a level of cells infected by chytrids is at least 10%. In some embodiments, the culture of *Haematococcus* cells may be contacted with salt when a level of cells infected by chytrids is at least 20%. In some embodiments, the culture of *Haematococcus* cells may be contacted with salt when a level of cells infected by chytrids is at least 30%. In some embodiments, the culture of *Haematococcus* cells may be contacted with salt when a level of cells infected by chytrids is at least 40%. In some embodiments, the culture of *Haematococcus* cells may be contacted with salt when a level of cells infected by chytrids is at least 50%.

In another non-limiting embodiment, a method of preventing a chytrid infection in a culture of *Haematococcus* may comprise: culturing a population of *Haematococcus* cells in a liquid culture medium; determining a number of *Haematococcus* cells infected with chytrids in the culture; contacting the culture with an effective amount of hydrogen peroxide when the percentage of *Haematococcus* cells infected with chytrids is less than a threshold level of the total cells; continuing to culture the *Haematococcus* cells; and verifying that a percentage of *Haematococcus* cells infected with chytrids is less than a threshold level of the total cells after contact with the hydrogen peroxide.

In some embodiments, the threshold level of cells infected with chytrids may be 1% of the total cells. In some embodiments, the threshold level of cells infected with chytrids may be 2% of the total cells. In some embodiments, the threshold level of cells infected with chytrids may be 3% of the total cells. In some embodiments, the threshold level of cells infected with chytrids may be 4% of the total cells. In some embodiments, the threshold level of cells infected with chytrids may be 5% of the total cells. In some embodiments, the threshold level of cells infected with chytrids may be 10% of the total cells. In some embodiments, the threshold level of cells infected with chytrids may be 15% of the total cells. In some embodiments, the threshold level of cells infected with chytrids may be 20% of the total cells. In some embodiments, the threshold level of cells infected with chytrids may be 25% of the total cells. In some embodiments, the threshold level of cells infected with chytrids may be 30% of the total cells.

In another non-limiting embodiment, a method of preventing and/or treating lysis in a culture of *Haematococcus* may comprise: culturing a population of *Haematococcus* cells in a liquid culture medium in growth conditions to obtain a culture of *Haematococcus* cells in which the cells are primarily (i.e., at least 80%) in the green swimmer stage; contacting the primarily green swimmer cell stage culture with an effective amount of hydrogen peroxide prior to the formation of cell cysts; and continuing to culture the *Haematococcus* cells in growth conditions.

In some embodiments, the method may further comprise determining a level of lysis in the culture of *Haematococcus* cells as a percentage of the total cells in the culture. In some embodiments, the culture of *Haematococcus* cells may be contacted with hydrogen peroxide when the level of lysis is less than 30%. In some embodiments, the culture of *Haematococcus* cells may be contacted with hydrogen peroxide when the level of lysis is less than 25%. In some embodiments, the culture of *Haematococcus* cells may be contacted with hydrogen peroxide when the level of lysis is less than 20%. In some embodiments, the culture of *Haematococcus* cells may be contacted with hydrogen peroxide when the level of lysis is less than 15%. In some embodiments, the culture of *Haematococcus* cells may be contacted with hydrogen peroxide when the level of lysis is less than 10%. In some embodiments, the culture of *Haematococcus* cells may be contacted with hydrogen peroxide when the level of lysis is less than 5%. In some embodiments, the culture of *Haematococcus* cells may be contacted with hydrogen peroxide when the level of lysis is less than 4%. In some embodiments, the culture of *Haematococcus* cells may be contacted with hydrogen peroxide when the level of lysis is less than 3%. In some embodiments, the culture of *Haematococcus* cells may be contacted with hydrogen peroxide when the level of lysis is less than 2%. In some embodiments, the culture of *Haematococcus* cells may be contacted with hydrogen peroxide when the level of lysis is less than 1%. In some embodiments, the culture of *Haematococcus* cells may be contacted with hydrogen peroxide when the level of lysis is 0%.

In some embodiments, the level of lysis in the culture may be maintained at or below the level of lysis at the time of contact with hydrogen peroxide while continuing to culture the *Haematococcus* cells in growth conditions. In some embodiments, the lysis level of the culture after contact with hydrogen peroxide may be 1-80% less than a lysis level in a control culture not receiving treatment with hydrogen peroxide. In some embodiments, the lysis level of the culture after contact with hydrogen peroxide may be 1-3% less than a lysis level in a control culture not receiving treatment with hydrogen peroxide. In some embodiments, the lysis level of the culture after contact with hydrogen peroxide may be 3-6% less than a lysis level in a control culture not receiving treatment with hydrogen peroxide. In some embodiments, the lysis level of the culture after contact with hydrogen peroxide may be 6-10% less than a lysis level in a control culture not receiving treatment with hydrogen peroxide. In some embodiments, the lysis level of the culture after contact with hydrogen peroxide may be 10-20% less than a lysis level in a control culture not receiving treatment with hydrogen peroxide. In some embodiments, the lysis level of the culture after contact with hydrogen peroxide may be 20-40% less than a lysis level in a control culture not receiving treatment with hydrogen peroxide. In some embodiments, the lysis level of the culture after contact with hydrogen peroxide may be 40-60% less than a lysis level in a control culture not receiving treatment with hydrogen peroxide. In some embodiments, the lysis level of the culture after contact with hydrogen peroxide may be 60-80% less than a lysis level in a control culture not receiving treatment with hydrogen peroxide.

In some embodiments, the method may comprise determining a live bacteria count in the culture of *Haematococcus* cells. In some embodiments, the live bacteria count may be reduced by $10-25\times10^5$ CFU/mL after contact with the hydrogen peroxide. In some embodiments, the live bacteria count may be reduced by $10-15\times10^5$ CFU/mL after contact with the hydrogen peroxide. In some embodiments, the live bacteria count may be reduced by $15-20\times10^5$ CFU/mL after contact with the hydrogen peroxide. In some embodiments, the live bacteria count may be reduced by $20-25\times10^5$ CFU/mL after contact with the hydrogen peroxide. In some embodiments, the live bacteria count may be maintained below $10^7$ CFU/mL following contact with the hydrogen peroxide.

In another non-limiting embodiment, a method of preventing lysis in a culture of *Haematococcus* may comprise: culturing a population of *Haematococcus* cells in a liquid culture medium in growth conditions to obtain a culture of *Haematococcus* cells in which the cells are primarily (i.e., at least 80%) in the green swimmer stage; determining a level of cell lysis for the *Haematococcus* cells; contacting the primarily green swimmer cell stage culture with an effective amount of hydrogen peroxide prior to the formation of cell cysts when the lysis level of the *Haematococcus* cells is less than a threshold level; continuing to culture the *Haematococcus* cells in growth conditions; and verifying that the level of lysis of *Haematococcus* cells is less than the threshold level after contact with the hydrogen peroxide.

In some embodiments, the threshold lysis level may be 1% of the total cells. In some embodiments, the threshold lysis level may be 2% of the total cells. In some embodiments, the threshold lysis level may be 3% of the total cells. In some embodiments, the threshold lysis level may be 4% of the total cells. In some embodiments, the threshold lysis level may be 5% of the total cells. In some embodiments, the threshold lysis level may be 10% of the total cells. In some embodiments, the threshold lysis level may be 15% of the total cells. In some embodiments, the threshold lysis level may be 20% of the total cells. In some embodiments, the threshold lysis level may be 25% of the total cells. In some embodiments, the threshold lysis level may be 30% of the total cells.

In some embodiments, the described methods may be applied to an open culture of *Haematococcus*. In some embodiments, the described methods may be applied to an outdoor culture of *Haematococcus*. In some embodiments, the described methods may be applied to a closed culture of *Haematococcus*. In some embodiments, the described methods may be applied to an indoor culture of *Haematococcus*.

The use of hydrogen peroxide and/or salt in the described methods does not function as a further stress to the *Haematococcus* cells for the accumulation of astaxanthin, but rather provides the function of prevention and treatment of lysis and chytrid infections to increase the survival of the *Haematococcus* cells. The application of the described methods to a culture of *Haematococcus* in a batch process also does not provide the necessary time period to adapt the *Haematococcus* cells for increased resistance to lysis or fungal infections, which would require many applications over multiple generations coupled with selection of the positively performing cells.

The level of lysis, level of chytrid infection, and stage of the *Haematococcus* cells may be assessed by means known in the art such as, but not limited to, visual observation under a microscope, or automated monitoring with cameras and visual recognition software, spectrometers, or fluorimeters. The monitoring and detection of the *Haematococcus* culture, whether manual or automated, may be used to determine when the hydrogen peroxide and/or salt of the described methods is administered to a culture by manual means, automated means, and combinations thereof. Automated monitoring and detection data may also be recorded or utilized by a programmable logic controller to control the application of hydrogen peroxide and/or salt to a culture of cells. Visual observation under a microscope of the *Haematococcus* cultures using the described methods in tests also showed that the methods aided in breaking up filamentous fungus and lowering the background bacteria population of the culture, which may contribute to lysis.

In some embodiments, a microalgae culture composition may comprise: a population of *Haematococcus* cells in a liquid culture medium; and a calculated concentration of hydrogen peroxide in the range of 0.005-0.025 mL of hydrogen peroxide per L of culture medium (mL/L), wherein the hydrogen peroxide has been added to the culture medium in the previous 120 minutes. In further embodiments, the culture may comprise a concentration of 1-20 ppt of sodium chloride. In some embodiments, the *Haematococcus* cells of the culture composition may be primarily (i.e., at least 80%) in the green swimmer stage. In some embodiments, the *Haematococcus* cells of the culture composition may be primarily (i.e., at least 80%) in the red cyst stage.

EXAMPLES

Embodiments of the invention are exemplified and additional embodiments are disclosed in further detail in the following Examples, which are not in any way intended to limit the scope of any aspects of the invention described herein. Within these Examples two different strains of *Haematococcus pluvialis* were tested and are identified as "Strain 1" and "Strain 2", respectively.

Example 1

Experiments were conducted to determine the degradation rate of hydrogen peroxide in a culture of *Haematococcus pluvialis*. An Amplex Red Hydrogen Peroxide Kit (CAT. No. A22188), commercially available from Life Technologies (Grand Island, N.Y.), was used to assay hydrogen peroxide concentrations according to the detection of a fluorescent product formed in the oxidation of a reagent in the presence of hydrogen peroxide. Samples of *Haematococcus pluvialis* (Strain 1) were taken from cultures in a carboy bioreactor (axenic conditions) and an open raceway pond bioreactor disposed in a greenhouse with paddlewheel mixing (non-axenic conditions). Samples from both cultures were dosed with 0.06 mL/L of hydrogen peroxide 25% stock concentration (effective concentration of 0.015 mL/L), and the hydrogen peroxide concentration was monitored every 30 minutes for 180 minutes using the Amplex Red Hydrogen Peroxide Kit. Samples from both cultures showed an exponential decay in the concentration of hydrogen peroxide, resulting in a concentration below a level that is expected to be effective against uniflagellates (e.g., fungi zoospores) [namely greater than 0.03 mL/L of 25% stock (calculated concentration greater than 0.0075 mL/L)] after 30 minutes, and an concentration of below detectable limits in 120 minutes. These results show that treating a culture with an calculated concentration of hydrogen peroxide of 0.015 mL/L will maintain a concentration above the levels expected to be effective against contamination (e.g., uniflagellates) in the short term (i.e., <30 minutes) and will thereafter dissipate to levels that are not harmful to any of the desired microorganisms in the culture, including the *Haematococcus* cells. The results also demonstrate that repeated doses of hydrogen peroxide over time do not create the risk of building up a residual concentration that would be harmful to the *Haematococcus* or detectable in the harvested end product.

Example 2

Experiments were conducted to evaluate the level of hydrogen peroxide tolerance of *Haematococcus pluvialis*. Green swimmer cells of a first strain of *Haematococcus pluvialis* (Strain 1) were tested in well plates by adding a single dose (0.06, 0.10, 0.13, 0.16 mL/L) of hydrogen peroxide 25% stock concentration to 2 mL cultures of cells. The calculated concentrations of the hydrogen peroxide doses tested were 0.0150, 0.0250, 0.0325, and 0.0400 mL/L. The amount of cell lysis was quantified using visual observation under a microscope 18 hours after administration of hydrogen peroxide. The results are presented in Table 1, with standard error denoted as "SE".

TABLE 1

| $H_2O_2$ dosage calculated concentration (mL/L) | % Cell Lysis at 18 hours (±1 SE) |
|---|---|
| 0.00 (control) | 0.8% ± 0.3% |
| 0.0150 | 1.6% ± 1% |
| 0.0250 | 1.9% ± 0.2% |
| 0.0325 | 2% ± 0.07% |
| 0.0400 | 5.2% ± 0.48% |

As shown in Table 1, significant lysis (i.e., more than 5%) of the cells occurred at hydrogen peroxide dosage levels above 0.0325 mL/L calculated concentration.

Green swimmer and red cyst cells of a second strain of *Haematococcus pluvialis* (Strain 2) were tested in well plates by adding a dose (0.03, 0.04, 0.05, 0.06, 0.07 mL/L) of hydrogen peroxide 35% stock concentration to 2 mL cultures of cells of both green swimmer cells and red cyst cells three times per day (i.e., morning, noon and evening). The calculated concentrations of the hydrogen peroxide doses tested were 0.0105, 0.0140, 0.0175, 0.0210, and 0.0245 mL/L. The amount of cell lysis was quantified using visual observation under a microscope after 24, 48, and 72 hours. The results are presented in Tables 2-3, with standard error denoted as "SE".

TABLE 2

| Green Swimmer Cells $H_2O_2$ dosage calculated concentration (mL/L) | % Cell lysis at time periods (h) after dosing (±1 SE) | | |
|---|---|---|---|
| | 24 | 48 | 72 |
| 0.00 (control) | 3.3% ± 1.7% | 5.0% ± 1.7% | 5.0% ± 0.0% |
| 0.0105 | 3.3% ± 1.7% | 5.0% ± 1.7% | 3.3% ± 0.0% |
| 0.0140 | 4.2% ± 0.8% | 5.8% ± 2.5% | 9.2% ± 4.2% |
| 0.0175 | 2.5% ± 0.8% | 9.2% ± 2.5% | 13.3% ± 3.3% |
| 0.0210 | 4.2% ± 2.5% | 6.7% ± 1.7% | 20.0% ± 3.3% |
| 0.0245 | 15.0% ± 0.0% | 22.5% ± 0.8% | 27.5% ± 2.5% |

TABLE 3

| Red Cyst Cells $H_2O_2$ dosage calculated concentration (mL/L) | % Cell lysis at time periods (h) after dosing (±1 SE) | | | |
|---|---|---|---|---|
| | 24 | 48 | 72 | 96 |
| 0.00 (control) | 1.7% ± 1.0% | 0.0% ± 0.0% | 0.8% ± 0.8% | 2.5% ± 0.8% |
| 0.0140 | 1.7% ± 1.0% | 0.8% ± 0.8% | 3.3% ± 0.0% | 3.3% ± 1.7% |
| 0.0175 | 1.1% ± 0.6% | 3.3% ± 1.7% | 5.8% ± 5.8% | 5.8% ± 2.5% |
| 0.0210 | 3.9% ± 2.0% | 0.8% ± 0.8% | 1.7% ± 0.0% | 18.3% ± 1.7% |
| 0.0245 | 3.9% ± 0.6% | 5.0% ± 1.7% | 9.2% ± 0.8% | 51.7% ± 5.0% |

As shown in Table 2, the green swimmer cells maintained a cell lysis level below 10% when dosed with hydrogen peroxide at a 0.0105 mL/L calculated concentration for at least 72 hours. At a calculated concentration of 0.0210 mL/L the green swimmer cells maintained lysis levels below 10% for 48 hours. These results show that the cells treated with lower concentration doses experienced low levels of lysis (i.e., below 10%) for all time periods, but the cultures receiving higher concentration doses only maintained low levels of lysis (i.e., below 10%) for 48 hours or less, thus indicating that the concentration of hydrogen peroxide in the method is critical and simply adding more does not equate to better results regarding lysis in green swimmer cells.

As shown in Table 3, the red cyst cells maintained a cell lysis level below 10% at dosages of hydrogen peroxide below 0.0175 mL/L calculated concentration for at least 96 hours, but dosages at or above 0.0175 mL/L calculated concentration experienced cell lysis above 10% after 48-96 hours. These results also show that simply increasing the dosages of hydrogen peroxide does not produce better results with regards to lysis in red cyst cells, however the results were not exactly the same for the concentrations when applied to green swimmer and red cyst cells. Therefore, the results of Table 2 and Table 3 together demonstrate the state of the cell, concentration of hydrogen peroxide, and the length of time the treatment is applied are factors that should be considered when hydrogen peroxide is used to treat a culture of *Haematococcus pluvialis* to maintain cell lysis at acceptable levels or prevent lysis.

Example 3

A series of *Haematococcus pluvialis* (Strain 1) cultures were compared using bacterial community sequencing (SSU rRNA 16s) to analyze the bacterial community of the cultures during a lysis event, a chytrid infection, and during treatment with hydrogen peroxide to determine if the bacteria community shifts or produces a detectable pattern.

*Haematococcus pluvialis* cultures containing green swimmer cells in open raceway pond bioreactors [identification numbers (#) 2210 and 2220] disposed in a greenhouse, using paddlewheel mixing, and operating in conditions: reactor volume of 16,000 L; Daily photosynthetically active radiation (PAR) of 57 mol m$^{-2}$ d$^{-1}$; pH of 7.5; and paddlewheel speed of 40%; were inoculated on the same day and cultured in growth conditions. The culture in bioreactor #2210 was not treated with hydrogen peroxide before or after transfer to bioreactor #2310. The culture in the bioreactor #2220 was treated every 24 hours with 0.03 mL/L of hydrogen peroxide 25% stock concentration (calculated concentration of 0.0075 mL/L) before and after the culture was transferred to open raceway pond bioreactor #2320 operating in conditions: reactor volume of 50,000 L; Daily PAR of 54 mol m$^{-2}$ d$^{-1}$; pH of 7.5; and paddlewheel speed of 40%; which was also disposed in a greenhouse and used paddlewheel mixing. The results showed that the treated culture in bioreactor #2220 retained high motility (95%) one day longer than the untreated culture in bioreactor #2210, and chytrids were detected three days later in the treated culture in bioreactor #2320 than they did in the untreated culture of bioreactor #2310.

Nitrogen fixing bacteria including *Rhizobium, Emticicia,* and *Sinorhizobium*, were identified as dominant species in the bacterial community analysis of the cultures and were present in the beginning and middle of the culture period for each culture. However, the relative amount of nitrogen fixing bacteria decreased from 20-40% to less than 10% of the dominant bacterial community, after the hydrogen peroxide treatments in bioreactor #2320. High amounts of cell lysis were visually observed in the treated culture (bioreactor #2320), but not until five days after the treatment ended. *Runella* was dominant in the bacterial community of the culture in bioreactor #2320 starting before the second hydrogen peroxide treatment and during the period of the lysis event.

A *Haematococcus pluvialis* culture containing green swimmer cells in an open raceway pond bioreactor #2330 disposed in a greenhouse, using paddlewheel mixing, and operating in conditions: reactor volume of 55,000 L; Daily PAR of 55 mol m$^{-2}$ d$^{-1}$; pH of 7.5; and paddlewheel speed of 40%; was treated once with 0.03 mL/L hydrogen peroxide 25% stock concentration (calculated concentration of 0.0075 mL/L) two days before transfer and twice after transfer to open raceway bioreactor #2430, which was disposed in a greenhouse, using paddlewheel mixing, and operating in conditions: reactor volume of 140,000 L; Daily PAR of 55 mol m$^{-2}$ d$^{-1}$; pH of 7.3; and paddlewheel speed of 70%. High amounts of cell lysis were visually observed before the first treatment and remained high for 4 days. The effect of the hydrogen peroxide treatment to prevent or decrease lysis appeared to be limited due to the fact that treatment began after the lysis had occurred. Chytrid sporangia were not detected in the culture. *Rheinheirmera, Flectobacillus, Runella*, and *Flavobacterium*, began increasing in relative to other bacteria in the bacterial community analysis of the culture during the start of lysis, however only *Runella* became dominant towards the end of the lysis period.

Another *Haematococcus pluvialis* culture containing green swimmer cells in open raceway pond bioreactor #2330 operating in conditions: reactor volume of 60,000 L; Daily PAR of 57 mol m$^{-2}$ d$^{-1}$; pH of 7.5; and paddlewheel speed of 40%; was treated twice with 0.03 mL/L hydrogen peroxide 25% stock concentration (calculated concentration of 0.0075 mL/L) before transfer to another bioreactor. The culture of bioreactor #2330 was transferred to open raceway pond bioreactor #2420 disposed in a greenhouse, using paddlewheel mixing, and operating in conditions: reactor volume of 140,000 L; Daily PAR of 58 mol m$^{-2}$ d$^{-1}$; pH of 7.3; and paddlewheel speed of 70%); but the culture was not treated after the transfer. This culture was observed to continue cell division after transfer to bioreactor #2420. Observations showed that motility decreased by about 30% after the first treatment and 60% lysis occurred after the second treatment. Chytrid sporangia were observed to be present at the end of the culture period, 7 days after hydrogen peroxide treatment ended. Bacteria including *Pseudomonas, Flectobacillus*, and *Cytophaga* were present in the bacterial community in both the bioreactors #2330 and #2420. The percentage of carotenoids in the culture was approximately 3.5%, quantified by UV method.

Example 4

An experiment was conducted to determine if treating a culture of *Haematococcus pluvialis* with hydrogen peroxide affects the live bacteria count. Cultures of *Haematococcus pluvialis* (Strain 1) containing green swimmer cells in open raceway ponds (250 L volume) with paddlewheel mixing and disposed in a warehouse were split into open pond bioreactors #2210 and 2230 disposed inside a greenhouse, using paddlewheel mixing, and operating in conditions: reactor volume of 16,000 L; Daily PAR of 50 mol m$^{-2}$ d$^{-1}$; pH of 7.5; and paddlewheel speed of 40%. The culture in bioreactor #2210 was treated with 0.33 mL/L hydrogen peroxide 3% stock concentration (calculated concentration of 0.0099 mL/L) every 6 hours for the duration of the culture's green swimmer stage (90 hours). The culture in bioreactor #2230 was not treated to serve as a control for comparison. Samples were taken to assess motility, lysis, and the live bacteria count in the cultures at 11, 34, 52, and 66 hours. The live bacteria count was obtained by plate count using Petrifilm available from 3M (St. Paul, Minn.), and the results are shown in Table 4.

TABLE 4

| | Live Bacteria Count (CFU/mL BacT) | |
|---|---|---|
| Time (h) | Untreated Control | $H_2O_2$ treatment |
| 11 | $3.7 \times 10^7$ | $4.8 \times 10^5$ |
| 34 | $1.0 \times 10^6$ | $5.5 \times 10^6$ |
| 52 | $1.5 \times 10^6$ | $1.8 \times 10^5$ |
| 66 | $2.9 \times 10^6$ | $4.5 \times 10^5$ |
| 90 | $8.1 \times 10^5$ | No data |

Motility was maintained above 60% for the entire experiment but was slightly higher in the untreated control culture. Lysis greater than 15% did not occur in either culture. As shown in Table 4, the culture that received the hydrogen peroxide treatment had an approximately 1 log reduction in the bacteria count. This result may be useful in analyzing the potential for lysis in the culture, as findings from previous experiments showed a correlation between bacteria concentrations above $10^7$ cells/mL and the occurrence of lysis in cultures of *Haematococcus pluvialis*. Therefore, reducing the live bacteria count of a *Haematococcus pluvialis* culture with a hydrogen peroxide treatment can be used to prevent conditions that are favorable for lysis and reduce the risk of losing *Haematococcus pluvialis* cells to lysis.

Example 5

A series of experiments were conducted to determine if treating a culture of *Haematococcus pluvialis* with hydrogen peroxide prevents lysis. Samples of a culture of *Haematococcus pluvialis* (Strain 1) containing green swimmer cells were taken from open raceway pond bioreactor #2330 disposed in a greenhouse, using paddlewheel mixing, and operating in conditions: reactor volume of 60,000 L; Daily PAR of 57 mol $m^{-2} d^{-1}$; pH of 7.5; and paddlewheel speed of 40%; before the culture was transferred to open raceway pond bioreactor #2430 disposed in a greenhouse, using paddlewheel mixing, and operating in conditions: reactor volume of 140,000 L; Daily PAR of 58 mol $m^{-2} d^{-1}$; pH of 7.3; and paddlewheel speed of 70%); as well as 24 and 48 hours after transfer to bioreactor #2430. The samples were divided into flasks with some flasks receiving treatment with 0.028 mL/L hydrogen peroxide 25% stock concentration (calculated concentration of 0.007 mL/L) three times per day, and some flasks receiving no treatment to serve as controls for comparison. Lysis was quantified daily through visual observation of samples under a microscope. The results are shown in Tables 5-7, with standard deviation denoted as "SD".

TABLE 5

| | % Lysis in samples from Bioreactor # 2330 (±1 SD) | |
|---|---|---|
| Time (h) | Untreated Control | $H_2O_2$ Treatment |
| 0 | 8.3 ± 7.6% | 8.3 ± 7.6% |
| 24 | 6.7 ± 2.4% | 10.0 ± 4.7% |
| 48 | 4.2 ± 3.5% | 12.5 ± 3.5% |
| 72 | 0.0 ± 0.0% | 0.0 ± 0.0% |
| 120 | 1.7 ± 0.0% | 0.8 ± 1.2% |

TABLE 6

| | % Lysis in samples from Bioreactor # 2430 24 hours after transfer (±1 SD) | |
|---|---|---|
| Time (h) | Untreated Control | $H_2O_2$ Treatment |
| 0 | 0.0 ± 0.0% | 0.0 ± 0.0% |
| 24 | 85.8 ± 3.5% | 7.5 ± 1.2% |
| 48 | 75.8 ± 20.0% | 0.0 ± 0.0% |
| 96 | 13.3 ± 4.7% | 4.1 ± 1.2% |

TABLE 7

| | % Lysis in samples from Bioreactor # 2430 48 hours after transfer | |
|---|---|---|
| Time (h) | Untreated Control | $H_2O_2$ Treatment |
| 0 | 3.3 ± 2.9% | 3.3 ± 2.9% |
| 24 | 63.3 ± 2.4% | 25.0 ± 9.4% |
| 96 | 97.5 ± 1.2% | 16.7 ± 4.7% |

As shown in Table 5, lysis remained at low levels in both the control and hydrogen peroxide treatment cultures. The results in Tables 6 and 7 show lysis occurred at high levels (greater than 80%) in the control cultures and was held to lower levels with the hydrogen peroxide treatments (less than 30%), demonstrating a treatment with hydrogen peroxide may successfully reduce lysis by 60-80%.

The findings from the flask test samples were then applied to commercial scale cultures of *Haematococcus pluvialis* (Strain 1) containing green swimmer cells that were transferred from open raceway pond bioreactor #2310 disposed in a greenhouse, using paddlewheel mixing, and operating in conditions: reactor volume of 55,000 L; Daily PAR of 42 mol $m^{-2} d^{-1}$; pH of 7.5; and paddlewheel speed of 40%; to open raceway pond bioreactor #2420 disposed in a greenhouse, using paddlewheel mixing, operating in conditions: reactor volume of 140,000 L; Daily PAR of 40 mol $m^{-2} d^{-1}$; pH of 7.3; and paddlewheel speed of 70%. Similarly, the culture in bioreactor #2320, operating in conditions: reactor volume of 60,000 L; Daily PAR of 42 mol $m^{-2} d^{-1}$; pH of 7.5; and paddlewheel speed of 40%; was transferred by being split into pond bioreactors #2410 and 2430 operating in conditions: reactor volume of 150,000 L; Daily PAR of 40 mol $m^{-2} d^{-1}$; pH of 7.3; and paddlewheel speed of 70%. The cultures in pond bioreactors #2310 and 2320 had previously received treatments of 0.02 mL/L hydrogen peroxide 35% stock concentration (calculated concentration of 0.007 mL/L) every six hours, which continued after the cultures were transferred until the fourth day of treatment. Lysis was quantified upon harvest of the culture through visual observation of samples under a microscope. Carotenoid content of the cells was measured by UV method upon harvest, and the average growth rate of the culture was calculated based on periodic dry weight samples. The results were compared to data from previous culture runs in the same bioreactors or bioreactors with similar operating conditions during the same month (September 2014) at the same location. The results are shown in Tables 8-10.

TABLE 8

| Bioreactor | H$_2$O$_2$ Treatment | Maximum % Lysis of Culture |
|---|---|---|
| 2410 | No | 25% |
| 2420 | No | 25% |
| 2430 | No | 90% |
| 2440 | No | 95% |
| 2410 | Yes | 70% |
| 2420 | Yes | 20% |
| 2430 | Yes | 35% |

TABLE 9

| Bioreactor | H$_2$O$_2$ Treatment | Maximum % Carotenoid (UV) |
|---|---|---|
| 2410 | No | 2.84 |
| 2420 | No | 0.79 |
| 2430 | No | 1.88 |
| 2440 | No | 2.38 |
| 2410 | Yes | 3.22 |
| 2420 | Yes | 3.58 |
| 2430 | Yes | 1.21 [Ended early] |

TABLE 10

| Bioreactor | H$_2$O$_2$ Treatment | Average Growth Rate (g/m$^2$/day) |
|---|---|---|
| 2410 | No | 2.1 |
| 2420 | No | 2.3 |
| 2430 | No | 3.2 |
| 2440 | No | 3.6 |
| 2410 | Yes | 4.7 |
| 2420 | Yes | 4.3 |
| 2430 | Yes | 2.3 [Ended early] |

As shown in Table 8, lysis remained in the range of 20-35% in two of the commercial scale cultures treated with hydrogen peroxide, which was an improvement over the historical data that showed untreated cultures may reach lysis levels over 80%. As shown in Tables 9 and 10, the cultures treated with hydrogen peroxide produced the higher levels of carotenoids and had a higher average growth rate than the untreated cultures, indicating that the hydrogen peroxide treatment may be directly improving growth and carotenoid accumulation or may be indirectly improving growth and carotenoid accumulation by creating an environment with suppressed lysis. Viewing the results from the flask tests and the commercial scale cultures together, treating a culture of *Haematococcus pluvialis* green swimmer cells with hydrogen peroxide at a calculated concentration of at least 0.007 mL/L every 6 hours can reduce the level of cell lysis by at least 60% without negatively affecting the culture growth rate (i.e., biomass accumulation) and accumulation of carotenoids.

Example 6

A series of experiments were conducted to evaluate the effectiveness of hydrogen peroxide alone and in combination with concentrations of salt as a treatment for controlling chytrid infections in *Haematococcus pluvialis* cultures. Culture samples of *Haematococcus pluvialis* (Strain 1) cultures were taken and placed into flasks from open raceway bioreactor #2420 disposed within a greenhouse, mixed with paddlewheels, and operating in conditions: reactor volume of 170,000 L; Daily PAR of 53 mol m$^{-2}$ d$^{-1}$; pH of 7.3; and paddlewheel speed of 70%. Bioreactor #2420 had just been inoculated with cells in the green swimmer stage into reddening conditions that comprised of culture medium comprising a 1 ppt concentration of sodium chloride (NaCl). The flask experiment consisted of duplicate untreated controls and duplicate treatments. The treated flask cultures were dosed with 0.03 mL/L hydrogen peroxide of 25% stock concentration (calculated concentration of 0.0075 mL/L) 2-3 times per day. Samples were taken from the flask cultures daily to monitor the percentage of chytrids in the total cells of the culture (% chytrid infection) through visual observation using a microscope and measurement of cell dry weight in g/L for a duration of about 9 days (217 hours). The results are shown in Tables 11-12.

TABLE 11

| | Average Chytrid Infection (%) | |
|---|---|---|
| Time (h) | Control | H$_2$O$_2$ Treatment |
| 0 | 0.0 ± 0.0% | 0.0 ± 0.0% |
| 24 | 0.0 ± 0.0% | 0.0 ± 0.0% |
| 48 | 0.8 ± 1.2% | 0.0 ± 0.0% |
| 72 | 0.0 ± 0.0% | 0.0 ± 0.0% |
| 144 | 38.3 ± 54.2% | 0.0 ± 0.0% |
| 168 | 40.0 ± 56.6% | 0.0 ± 0.0% |
| 197 | 43.3 ± 44.8% | 0.0 ± 0.0% |
| 217 | 50.0 ± 58.9% | 0.0 ± 0.0% |

TABLE 12

| | Average Cell Dry Weight (g/L) | |
|---|---|---|
| Time (h) | Control | H$_2$O$_2$ Treatment |
| 0 | 0.1 ± 0.0 | 0.1 ± 0.0 |
| 24 | 0.1 ± 0.1 | 0.1 ± 0.0 |
| 48 | 0.3 ± 0.0 | 0.2 ± 0.0 |
| 72 | 0.5 ± 0.1 | 0.3 ± 0.1 |
| 144 | No data | No data |
| 168 | 0.8 ± 0.2 | 0.7 ± 0.0 |
| 197 | 0.7 ± 0.0 | 0.6 ± 0.0 |
| 217 | 0.9 ± 0.0 | 0.8 ± 0.0 |

Results showed that the % chytrid infection in the untreated controls varied widely (15-90%) starting on day six (144 h), with the average steadily increasing over the remaining days to over 40% (as shown in Table 11). In the treated cultures, % chytrid infection was 0% the entire nine day period. As shown in Table 12, the dry cell weight increased in both the control and treated cultures.

Culture samples for a second experiment were taken three days after inoculation when the salt concentration was at 1 ppt from open raceway bioreactor #2440 disposed within a greenhouse, mixed with paddlewheels, and operating in conditions: reactor volume of 175,000 L; Daily PAR of 40 mol m$^{-2}$ d$^{-1}$; pH of 7.3; paddlewheel speed of 70%. Samples were placed in flasks for culturing, consisting of duplicate untreated controls and duplicate treatments. The treated flask cultures were dosed with 0.03 mL/L hydrogen peroxide of 25% stock concentration (calculated concentration of 0.0075 mL/L) 2-3 times per day. The flask cultures contained *Haematococcus pluvialis* (Strain 1) cells in both the green swimmer stage and early red cyst stage. Samples were taken from the flask cultures daily to quantify % chytrid infection and cell dry weight for a duration of about 6 days (144 hours). The results are shown in Tables 13-14.

TABLE 13

| | Average Chytrid Infection (%) | |
|---|---|---|
| Time (h) | Control | H$_2$O$_2$ Treatment |
| 0 | 0.0 ± 0.0% | 0.0 ± 0.0% |
| 24 | 0.0 ± 0.0% | 1.7 ± 2.9% |
| 96 | 59.4 ± 7.7% | 25.0 ± 2.9% |
| 120 | 68.3 ± 4.4% | 51.7 ± 5.0% |
| 144 | 67.2 ± 4.2% | 43.9 ± 4.2% |

TABLE 14

| | Average Cell Dry Weight (g/L) | |
|---|---|---|
| Time (h) | Control | H$_2$O$_2$ Treatment |
| 0 | 0.16 ± 0.00 | 0.16 ± 0.00 |
| 24 | 0.32 ± 0.05 | 0.31 ± 0.02 |
| 96 | 0.53 ± 0.05 | 0.55 ± 0.04 |
| 120 | 0.56 ± 0.16 | 0.49 ± 0.09 |
| 144 | No data | No data |

As shown in Table 13, the % chytrid infection reached 67% in the controls and was reduced in the treated cultures. As shown in Table 14, the dry cell weight increased in both the control and treated cultures.

Culture samples of *Haematococcus pluvialis* (Strain 1) for a third experiment were collected from open raceway bioreactor #2210 disposed within a greenhouse, mixed with a paddlewheel, and operating in conditions: reactor volume of 18,000 L; Daily PAR of 48 mol m$^{-2}$ d$^{-1}$; pH of 7.5; paddlewheel speed of 40%. The collected samples were inoculated in the green swimmer stage in growth conditions [i.e., in the absence of sodium chloride (NaCl)]. The samples were distributed in flasks, consisting of duplicate untreated controls and duplicate treatments. The treated flask cultures were dosed with 0.03 mL/L hydrogen peroxide of 25% stock concentration (calculated concentration of 0.0075 mL/L) two times per day. Samples were taken from the flask cultures daily to quantify % chytrid infection and cell dry weight for a duration of about 11 days (264 hours). The results are shown in Tables 15-16.

TABLE 15

| | Average Chytrid Infection (%) | |
|---|---|---|
| Time (h) | Control | H$_2$O$_2$ Treatment |
| 0 | 0.0 ± 0.0% | 0.0 ± 0.0% |
| 24 | 0.0 ± 0.0% | 0.0 ± 0.0% |
| 48 | 0.0 ± 0.0% | 0.0 ± 0.0% |
| 96 | 0.0 ± 0.0% | 0.0 ± 0.0% |
| 120 | 0.0 ± 0.0% | 0.0 ± 0.0% |
| 144 | 6.7 ± 9.4% | 4.2 ± 5.9% |
| 168 | 36.7 ± 37.1% | 18.3 ± 25.9% |
| 192 | 49.2 ± 29.5% | 26.6 ± 37.1% |
| 264 | 81.7 ± 2.4% | 51.7 ± 7.1% |

TABLE 16

| | Average Cell Dry Weight (g/L) | |
|---|---|---|
| Time (h) | Control | H$_2$O$_2$ Treatment |
| 0 | 0.26 ± 0.00 | 0.26 ± 0.00 |
| 24 | 0.93 ± 0.04 | 0.76 ± 0.06 |
| 48 | No data | No data |
| 96 | 2.16 ± 0.08 | 1.90 ± 0.00 |
| 120 | 2.31 ± 0.32 | 2.26 ± 0.00 |
| 144 | No data | No data |
| 168 | 2.20 ± 0.37 | 2.2 ± 0.00 |
| 192 | 2.73 ± 0.07 | 2.68 ± 0.91 |
| 264 | 2.19 ± 0.325 | 2.02 ± 0.65 |

As shown in Table 15, the % chytrid infection varied widely in the first 8 days (192 h), but was reduced in the treatments as compared to the control by day 11 (264 h). As shown in Table 16, the dry cell weight increased in both the control and treated cultures but was highly variable by the end of the experiment.

Culture samples of *Haematococcus pluvialis* (Strain 1) for a fourth experiment were collected from open raceway bioreactor #2310 disposed within a greenhouse, mixed with a paddlewheel, and operating in conditions: reactor volume of 48,000 L; Daily PAR of 50 mol m$^{-2}$ d$^{-1}$; pH of 7.5; and paddlewheel speed of 40%. The culture samples were inoculated in the green swimmer stage in growth conditions [i.e., in less than 1 ppt of sodium chloride (NaCl)]. The flask cultures were then diluted 3:1 with nitrate free HMB media and brought to a 1 ppt concentration of NaCl, consisting of duplicate untreated controls and duplicate treatments. The treated flask cultures were dosed with 0.03 mL/L hydrogen peroxide of 25% stock concentration (calculated concentration of 0.0075 mL/L) 3 times per day. Samples were taken from the flask cultures daily to % chytrid infection and cell dry weight for a duration of about 9 days (216 hours). The results are shown in Tables 17-18.

TABLE 17

| | Average Chytrid Infection (%) | |
|---|---|---|
| Time (h) | Control | H$_2$O$_2$ Treatment |
| 0 | 0.0 ± 0.0% | 0.0 ± 0.0% |
| 24 | 0.0 ± 0.0% | 0.0 ± 0.0% |
| 48 | 0.0 ± 0.0% | 0.0 ± 0.0% |
| 120 | 16.1 ± 3.5% | 1.7 ± 1.7% |
| 144 | 60.6 ± 7.5% | 18.3 ± 18.5% |
| 168 | 62.8 ± 12.5% | 17.2 ± 14.4% |
| 192 | 67.2 ± 5.4% | 32.2 ± 28.1% |
| 216 | 90.6 ± 5.4% | 44.4 ± 46.8% |

TABLE 18

| | Average Cell Dry Weight (g/L) | |
|---|---|---|
| Time (h) | Control | H$_2$O$_2$ Treatment |
| 0 | 0.00 ± 0.00 | 0.00 ± 0.00 |
| 24 | 0.45 ± 0.03 | 0.46 ± 0.07 |
| 48 | 0.96 ± 0.15 | 0.94 ± 0.18 |
| 120 | 1.71 ± 0.20 | 1.60 ± 0.05 |
| 144 | 1.29 ± 0.09 | 1.56 ± 0.35 |
| 168 | 1.55 ± 0.41 | 2.01 ± 0.02 |
| 192 | 1.21 ± 0.24 | 2.34 ± 0.39 |
| 216 | 1.77 ± 0.15 | 2.96 ± 0.26 |

As shown in Table 17, a 50-90% reduction in % chytrid infection in the treatments as compared to the control was observed starting 5 days after inoculation (144 h). The variability in the results were attributed to the fact that one treatment flask became infected while the other did not. As shown in Table 18, the dry cell weight increased in both the control and treated cultures but was higher in treated flasks.

Culture samples of *Haematococcus pluvialis* (Strain 1) were collected for a fifth experiment from open raceway bioreactor #2310 operating in conditions: reactor volume of 66,000 L; Daily PAR of 48 mol m$^{-2}$ d$^{-1}$; pH of 7.5; and paddlewheel speed of 40%. The culture samples were distributed into flasks for culturing, consisting of duplicate untreated controls and duplicate treatments. The flask cultures were then diluted 1:3 into reddening media comprising 1 ppt NaCl or 2 ppt NaCl (33.3 mL and 66.6 mL culture media). The treated flask cultures were dosed with 0.03 mL/L hydrogen peroxide of 25% stock concentration (calculated concentration of 0.0075 mL/L) 3 times per day. Samples were taken from the flask cultures daily to analyze % chytrid infection and cell dry weight for a duration of about 8 days (192 hours). The results are shown in Tables 19-20.

TABLE 19

Average Chytrid Infection (%)

| Time (h) | 1 ppt NaCl Control | 1 ppt NaCl and H$_2$O$_2$ Treatment | 2 ppt NaCl Control | 2 ppt NaCl and H$_2$O$_2$ Treatment |
| --- | --- | --- | --- | --- |
| 0 | 0.0 ± 0.0% | 0.0 ± 0.0% | 0.0 ± 0.0% | 0.0 ± 0.0% |
| 24 | 0.0 ± 0.0% | 0.0 ± 0.0% | 0.0 ± 0.0% | 0.0 ± 0.0% |
| 120 | 27.5 ± 20.0% | 0.0 ± 0.0% | 86.7 ± 2.4% | 0.0 ± 0.0% |
| 144 | 76.7 ± 9.4% | 0.0 ± 0.0% | 94.2 ± 5.9% | 0.0 ± 0.0% |
| 168 | 93.30 ± 7.1% | 0.0 ± 0.0% | 100.0 ± 0.0% | 0.0 ± 0.0% |
| 192 | 97.5 ± 1.2% | 0.0 ± 0.0% | 97.5 ± 1.2% | 0.0 ± 0.0% |

TABLE 20

Average Cell Dry Weight (g/L)

| Time (h) | 1 ppt NaCl Control | 1 ppt NaCl and H$_2$O$_2$ Treatment | 2 ppt NaCl Control | 2 ppt NaCl and H$_2$O$_2$ Treatment |
| --- | --- | --- | --- | --- |
| 0 | 0.03 ± 0.00 | 0.03 ± 0.00 | 0.03 ± 0.00 | 0.03 ± 0.00 |
| 24 | 1.16 ± 0.06 | 1.01 ± 0.04 | 1.12 ± 0.03 | 1.00 ± 0.06 |
| 120 | 1.33 ± 0.18 | 0.89 ± 0.01 | 1.12 ± 0.23 | 0.86 ± 0.06 |
| 144 | 0.95 ± 0.01 | 0.72 ± 0.06 | 0.58 ± 0.14 | 0.66 ± 0.08 |
| 168 | 0.64 ± 0.06 | 0.78 ± 0.03 | 0.60 ± 0.03 | 0.78 ± 0.03 |
| 192 | 0.91 ± 0.07 | 1.01 ± 0.04 | 0.66 ± 0.03 | 1.00 ± 0.03 |

As shown in Table 19, a chytrid infection appeared within 5 days (120 h) and increased to greater than 90% chytrid infection by day 7 (168 h) in the control cultures. In the treated cultures, % chytrid infection was 0% the entire eight day period. As shown in Table 20, the dry cell weight was comparable between control and treated cultures. Across all experiments, treatment with hydrogen peroxide was show to be effective in reducing chytrid infections when used with and without salt.

Example 7

An experiment was conducted to evaluate the effectiveness of the combination of salt and hydrogen peroxide as a treatment method of reducing chytrids in an infected culture of *Haematococcus pluvialis*. Culture samples of *Haematococcus pluvialis* (Strain 2) were collected from 3,000 L open raceway pond bioreactor #MP1 with paddlewheel mixing disposed outdoors. At the time the samples was taken, the culture comprised green swimmer cells and chytrids (100% of culture infected). One mL of infected culture was inoculated into replicate flasks (100 mL volume) containing axenic green swimmers from a carboy bioreactor culture diluted into reddening media 1 part culture to 3 parts media comprising either 1 or 3 ppt salt (NaCl). The flask cultures containing 1 ppt salt were dosed three times per day (morning, noon and evening) with 0.02 or 0.04 mL/L of hydrogen peroxide 35% stock concentration (calculated concentrations of 0.007 or 0.014 mL/L). The flask cultures containing 3 ppt salt were dosed three times per day (morning, noon and evening) with 0.02 mL/L of hydrogen peroxide 35% stock concentration (calculated concentration of 0.007 mL/L). The percent of the cells infected with chytrids was quantified via visual observation under a microscope at 72 and 96 hours after the cultures were inoculated in the flask. The results are shown in Table 21.

TABLE 21

% Chytrids Infection

| Time (h) | Untreated Control | 1 ppt salt & 0.007 mL/L H$_2$O$_2$ | 1 ppt salt & 0.0014 mL/L H$_2$O$_2$ | 3 ppt salt & 0.007 mL/L H$_2$O$_2$ |
| --- | --- | --- | --- | --- |
| 72 | 71.7 ± 0.0% | 57.5 ± 5.9% | 36.7 ± 4.7% | 72.5 ± 1.2% |
| 96 | 96.7 ± 4.7% | NO DATA | 97.5 ± 1.2% | NO DATA |

As shown in Table 21, the hydrogen peroxide treatments for the cultures containing 1 ppt salt showed a reduction in the chytrids infection % compared to the untreated control and treatment containing 3 ppt salt after 72 hours, with the 0.014 mL/L hydrogen peroxide treatment resulting in a larger reduction than the 0.007 mL/L hydrogen peroxide treatment. After 96 hours the 1 ppt salt and 0.014 mL/L hydrogen peroxide treatment did not appear to continue as an effective treatment for the reduction of chytrids, demonstrating that the combination of salt and hydrogen peroxide may be effective for reducing chytrids in a culture of *Haematococcus* with an existing infection for a limited period of time after which additional action may need to be taken in the form of harvesting the *Haematococcus* cells or utilizing a different treatment method.

Example 8

An experiment was conducted to evaluate the effectiveness of the combination of salt and hydrogen peroxide as a treatment method for reducing chytrids in an infected culture of *Haematococcus pluvialis*. Three 3,000 L open raceway pond bioreactor #'s MP1, MP2, & MP3 with paddlewheel mixing disposed outdoors were inoculated with cultures of green swimmer *Haematococcus pluvialis* (Strain 2) cells from outdoor reactor #2310 at a dilution ratio of 1 part culture samples to 3 parts reddening media containing 1 ppt salt (NaCl). After the cultures failed to become infected on their own, chytrid infection was promoted by adding 5 L of infected culture from another outdoor reactor (#2420) after 6 days. MP1 and MP3 received treatments of 0.03 mL/L of hydrogen peroxide 35% stock concentration (calculated concentration of 0.0105 mL/L) every 6 hours. MP2 was not treated with hydrogen peroxide to serve as an untreated control for comparison purposes. The percent of cells infected with chytrids was quantified using visual observation under a microscope 24 hours after the chytrids were introduced, and determined to be 20% in MP1, 10% in MP2, and less than 5% in MP3. After hydrogen peroxide treatments began, the percent of the cultures infected with chytrids, percent of carotenoids by UV method, and cell dry weight (g/L) were quantified daily. The results are show in Tables 22-24.

TABLE 22

| | % Chytrids Infection | | |
|---|---|---|---|
| Time (days after inoculation) | Untreated Control (MP2, initial infection 10%) | 0.0105 mL/L H₂O₂ (MP1, initial infection 20%) | 0.0105 mL/L H₂O₂ (MP3, initial infection less than 5%) |
| 5 | NO DATA | NO DATA | NO DATA |
| 6 | NO DATA | NO DATA | NO DATA |
| 7 | 8.3 ± 7.6% | 23.3 ± 5.8% | 1.7 ± 2.9% |
| 8 | 10.0 ± 5.0% | 20.0 ± 5.0% | 0.0 ± 0.0% |
| 9 | 16.7 ± 12.6% | 30.0 ± 10.0% | 1.7 ± 2.9% |
| 10 | 45.0 ± 18.0% | 26.7 ± 2.9% | 0.0 ± 0.0% |
| 11 | 76.7 ± 5.8% | 61.7 ± 24.7% | 0.0 ± 0.0% |
| 12 | 90.0 ± 10.0% | 63.3 ± 16.1% | 0.0 ± 0.0% |
| 13 | 95.0 ± 5.0% | 73.3 ± 7.6% | 3.3 ± 2.9% |
| 14 | 98.3 ± 2.9% | 76.7 ± 17.6% | 0.0 ± 0.0% |

TABLE 23

| | % Carotenoids (UV) | | |
|---|---|---|---|
| Time (days after inoculation) | Untreated Control (MP2, initial infection 10%) | 0.0105 mL/L H₂O₂ (MP1, initial infection 20%) | 0.0105 mL/L H₂O₂ (MP3, initial infection less than 5%) |
| 5 | NO DATA | NO DATA | NO DATA |
| 6 | NO DATA | NO DATA | NO DATA |
| 7 | NO DATA | NO DATA | NO DATA |
| 8 | 3.72 | 3.71 | 3.77 |
| 9 | 3.72 | 4.03 | 4.19 |
| 10 | 4.20 | 4.44 | 4.55 |
| 11 | 3.24 | 4.33 | 3.74 |
| 12 | 3.27 | 3.95 | 4.47 |
| 13 | NO DATA | NO DATA | NO DATA |
| 14 | NO DATA | NO DATA | NO DATA |

TABLE 24

| | Cell Dry Weight (g/L) | | |
|---|---|---|---|
| Time (days after inoculation) | Untreated Control (MP2, initial infection 10%) | 0.0105 mL/L H₂O₂ (MP1, initial infection 20%) | 0.0105 mL/L H₂O₂ (MP3, initial infection less than 5%) |
| 5 | 0.156 | 0.216 | 0.190 |
| 6 | 0.219 | 0.283 | 0.201 |
| 7 | 0.244 | 0.321 | 0.311 |
| 8 | 0.314 | 0.371 | 0.412 |
| 9 | 0.317 | 0.349 | 0.353 |
| 10 | 0.346 | 0.370 | 0.343 |
| 11 | 0.347 | 0.353 | 0.349 |
| 12 | 0.375 | 0.357 | 0.375 |
| 13 | 0.366 | 0.364 | 0.390 |
| 14 | 0.360 | 0.357 | 0.427 |

As shown in Table 22, the hydrogen peroxide and salt treatment was effective for maintaining the chytrids infection level below 5% in the MP3 culture which was below 5% when the treatments started. The hydrogen peroxide and salt treatment was also effective in slowing the chytrid infection of the MP1 culture which started with a moderate level (20%) as compared to the untreated control (MP2). Visual observation of the red cyst cells under a microscope also showed that the *Haematococcus* cells were susceptible to infection when the cells were transitioning from the green swimmer stage to the red cyst stage before the cyst had fully formed.

As shown in Tables 23 and 24, the continuous treatments with hydrogen peroxide in the presence of salt did not inhibit the accumulation of carotenoids and biomass in the *Haematococcus* cells. Together these results demonstrate that continuously treating a culture of *Haematococcus* cells infected by chytrids with hydrogen peroxide in the presence of low salt (1 ppt) is effective in preventing an increase in the infection if treatment is started when the infection is at a low level (below 5%), or at a minimum the treatment is effective in slowing down the increase in the infection that is already at a moderate level (e.g., 20%) at the time treatment is initiated without negatively affecting the carotenoid (e.g., astaxanthin) and biomass accumulation by *Haematococcus*.

Example 9

An experiment was conducted to evaluate if higher concentrations [greater than 0.03 mL/L 35% stock (calculated concentrations greater than 0.0105 mL/L)] of hydrogen peroxide could be used as a treatment method for reducing chytrids in an infected culture of *Haematococcus pluvialis*. Culture samples of *Haematococcus pluvialis* (Strain 2) were collected on day 5 of the culture from open raceway bioreactor #2420 operating in conditions: reactor volume of 170,000 L; Daily PAR not measured; pH of 7.3; and paddlewheel speed of 70%). Culture samples were distributed into flasks for culturing, consisting of duplicate untreated controls and duplicate treatments. Treatments compared different frequency doses (one to three times daily) of higher concentrations (0.04 and 0.05 mL/L) of hydrogen peroxide 35% stock concentration (calculated concentrations of 0.0140 and 0.0175 mL/L) with the standard treatment to date (calculated concentration of 0.0105 mL/L three times daily). Samples were taken from the flask cultures every few days in order to quantify % lysis, % chytrid infection, and cell dry weight for a duration of about 11 days. Due to lysis rates exceeding 10% in all treatments by day 5, treatment was discontinued and recovery from lysis was monitored. Results are shown in Table 25-27.

TABLE 25

| | % Lysis | | | | | |
|---|---|---|---|---|---|---|
| Time (days after inoculation) | Untreated Control | 0.0105 mL/L H₂O₂ 3 times per day | 0.0140 mL/L H₂O₂ 1 time per day | 0.0140 mL/L H₂O₂ 2 times per day | 0.0140 mL/L H₂O₂ 3 times per day | 0.0175 mL/L H₂O₂ 1 time per day |
| 0 | 4.2 ± 1.2 | 4.2 ± 1.2 | 4.2 ± 1.2 | 4.2 ± 1.2 | 4.2 ± 1.2 | 4.2 ± 1.2 |
| 3 | 0.8 ± 1.2 | 0.8 ± 1.2 | 5.0 ± 2.4 | 5.0 ± 4.7 | 2.5 ± 3.5 | 2.5 ± 1.2 |
| 4 | 4.2 ± 5.9 | 3.3 ± 2.4 | 4.2 ± 1.2 | 3.3 ± 2.4 | 9.2 ± 1.2 | 4.2 ± 1.2 |
| 5 | 1.7 ± 0.0 | 10.8 ± 1.2 | 10.0 ± 2.4 | 10.0 ± 2.4 | 42.5 ± 15.3 | 9.2 ± 1.2 |
| 6 | 0.0 ± 0.0 | 3.3 ± 2.4 | 7.5 ± 1.2 | 9.7 ± 5.9 | 55.0 ± 30.6 | 6.7 ± 2.4 |

TABLE 25-continued

| | | | % Lysis | | | |
|---|---|---|---|---|---|---|
| Time (days after inoculation) | Untreated Control | 0.0105 mL/L $H_2O_2$ 3 times per day | 0.0140 mL/L $H_2O_2$ 1 time per day | 0.0140 mL/L $H_2O_2$ 2 times per day | 0.0140 mL/L $H_2O_2$ 3 times per day | 0.0175 mL/L $H_2O_2$ 1 time per day |
| 9 | No Data | 6.7 ± 2.4 | 10.8 ± 1.2 | 5.0 ± 0.0 | 60.0 ± 28.3 | 6.7 ± 4.7 |
| 11 | No Data | 4.2 ± 3.5 | 7.5 ± 1.2 | 0.0 ± 0.0 | 56.7 ± 33.0 | 4.2 ± 3.5 |

TABLE 26

| | | | % Chytrid infection | | | |
|---|---|---|---|---|---|---|
| Time (days after inoculation) | Untreated Control | 0.0105 mL/L $H_2O_2$ 3 times per day | 0.0140 mL/L $H_2O_2$ 1 time per day | 0.0140 mL/L $H_2O_2$ 2 times per day | 0.0140 mL/L $H_2O_2$ 3 times per day | 0.0175 mL/L $H_2O_2$ 1 time per day |
| 0 | 0.0 ± 0.0 | 0.0 ± 0.0 | 0.0 ± 0.0 | 0.0 ± 0.0 | 0.0 ± 0.0 | 0.0 ± 0.0 |
| 3 | 28.3 ± 23.6 | 0.8 ± 1.2 | 0.0 ± 0.0 | 2.5 ± 1.2 | 3.3 ± 4.7 | 0.8 ± 1.2 |
| 4 | 41.7 ± 18.8 | 2.5 ± 3.5 | 0.0 ± 0.0 | 2.5 ± 3.5 | 0.0 ± 0.0 | 1.7 ± 0.0 |
| 5 | 53.3 ± 0.0 | 1.7 ± 0.0 | 1.7 ± 2.4 | 5.0 ± 4.7 | 0.0 ± 0.0 | 1.7 ± 0.0 |
| 6 | 88.3 ± 2.4 | 2.5 ± 1.2 | 2.5 ± 1.2 | 5.8 ± 3.5 | 0.0 ± 0.0 | 0.0 ± 0.0 |
| 9 | 97.5 ± 3.5 | 7.5 ± 3.5 | 0.0 ± 0.0 | 43.3 ± 4.7 | 0.0 ± 0.0 | 0.0 ± 0.0 |
| 11 | No Data | 100.0 ± 0.0 | 35.8 ± 29.5 | 97.5 ± 3.5 | 11.7 ± 16.5 | 34.2 ± 27.1 |

TABLE 27

| | | | Culture Dry Weight (g/L) | | | |
|---|---|---|---|---|---|---|
| Time (days after inoculation) | Untreated Control | 0.0105 mL/L $H_2O_2$ 3 times per day | 0.0140 mL/L $H_2O_2$ 1 time per day | 0.0140 mL/L $H_2O_2$ 2 times per day | 0.0140 mL/L $H_2O_2$ 3 times per day | 0.0175 mL/L $H_2O_2$ 1 time per day |
| 0 | 0.29 ± 0.02 | 0.29 ± 0.02 | 0.29 ± 0.02 | 0.29 ± 0.02 | 0.29 ± 0.02 | 0.29 ± 0.02 |
| 3 | 0.42 ± 0.07 | 0.42 ± 0.07 | 0.49 ± 0.05 | 0.44 ± 0.0 | 0.40 ± 0.01 | 0.47 ± 0.03 |
| 4 | No Data | No Data | No Data | No Data | No Data | No Data |
| 5 | No Data | No Data | No Data | No Data | No Data | No Data |
| 6 | No Data | 0.45 ± 0.02 | 0.44 ± 0.0 | 0.41 ± 0.11 | 0.30 ± 0.06 | 0.35 ± 0.02 |
| 9 | 0.59 ± 0.29 | 0.74 ± 0.02 | 0.82 ± 0.04 | 0.67 ± 0.01 | 0.54 ± 0.11 | 0.76 ± 0.01 |
| 11 | 0.57 ± 0.16 | 0.69 ± 0.09 | 0.54 ± 0.32 | 0.64 ± 0.08 | 0.81 ± 0.1 | 0.79 ± 0.13 |

As shown in Table 25, percent lysis reached 10% in all cultures treated with hydrogen peroxide by day 5, except for 0.014 mL/L dosed three times per day which were at 40% lysis. Treatment was discontinued at this time and the lysis rate remained stable through days 6 to 11. As shown in Table 26, chytrid infection increased to 100% in the untreated controls, but remained less than 10% in all treated flasks until 4-6 days after treatment ended. Final infection rates were lowest in flasks previously dosed with 0.0140 and 0.0175 mL/L once per day. As shown in Table 27, culture dry weights were highest in the cultures treated once daily on day 9. While the results showed that the treatments did not demonstrate a negative effect on lysis, the treatments were effective against chytrid infection without negatively affecting dry weight.

Example 10

A second flask experiment was conducted to evaluate if one daily treatment of 0.03-0.05 mL/L 35% stock concentration of hydrogen peroxide (calculated concentration 0.0105-0.0175 mL/L) could be used as a treatment method for reducing chytrids in an infected culture of *Haematococcus pluvialis*. Culture samples of *Haematococcus pluvialis* (Strain 2) were collected on the second day of the culture from open raceway bioreactor #2430 operating in conditions: reactor volume of 170,000 L; Daily PAR not measured; pH of 7.3; and paddlewheel speed of 70. The culture samples were distributed into flasks for culturing, consisting of duplicate untreated controls and duplicate treatments. Treatments compared different frequency doses (once daily and once daily followed by every other day) of 0.03, 0.04 and 0.05 mL/L 35% stock hydrogen peroxide (calculated concentrations of 0.0105, 0.0140, and 0.0175 mL/L). Samples were taken from the flask cultures daily to quantify % lysis and % chytrid infection and cell dry weight was quantified every other day for a duration of 11 days. The results are shown in Tables 28-30.

TABLE 28

| | | % Lysis | | | | |
|---|---|---|---|---|---|---|
| Time (days after inoculation) | Untreated Control | 0.0105 mL/L $H_2O_2$ 1 time per day | 0.0105 mL/L $H_2O_2$ 1 time per day for 3 d then every other day | 0.0140 mL/L $H_2O_2$ 1 time per day | 0.0140 mL/L $H_2O_2$ 1 time per day for 3 d then every other day | 0.0175 mL/L $H_2O_2$ 1 time per day for 2 d then every other |
| 0 | 0.8 ± 2.0 | 0.8 ± 2.0 | 0.8 ± 2.0 | 0.8 ± 2.0 | 0.8 ± 2.0 | 0.8 ± 2.0 |
| 3 | 1.7 ± 2.4 | 0.0 ± 0.0 | 0.0 ± 0.0 | 4.2 ± 1.2 | 4.2 ± 1.2 | 31.7 ± 11.8 |
| 4 | 0.0 ± 0.0 | 1.7 ± 0.0 | 1.7 ± 0.0 | 10.0 ± 8.7 | 10.0 ± 8.7 | 22.2 ± 8.5 |
| 5 | 0.0 ± 0.0 | 1.7 ± 0.0 | 1.7 ± 2.4 | 10.0 ± 2.4 | 15.8 ± 5.9 | 19.2 ± 17.6 |
| 6 | 0.0 ± 0.0 | 0.8 ± 2.0 | 3.3 ± 4.7 | 9.2 ± 3.5 | 6.7 ± 0.0 | 25 ± 0.0 |
| 7 | 1.7 ± 0.0 | 0.0 ± 0.0 | 0.0 ± 0.0 | 20.0 ± 9.4 | 13.3 ± 4.7 | No Data |
| 8 | 5.8 ± 1.2 | 1.7 ± 2.4 | 0.8 ± 1.2 | 6.7 ± 7.0 | 13.3 ± 2.4 | No Data |
| 9 | 0.8 ± 1.2 | 7.5 ± 8.3 | 0.8 ± 1.2 | 21.7 ± 7.1 | 5.0 ± 2.4 | No Data |
| 10 | 6.7 ± 2.4 | 0.0 ± 0.0 | 0.8 ± 1.2 | 9.2 ± 3.5 | 15.8 ± 12.9 | No Data |

TABLE 29

| | | % Chytrid infection | | | | |
|---|---|---|---|---|---|---|
| Time (days after inoculation) | Untreated Control | 0.0105 mL/L $H_2O_2$ 1 time per day | 0.0105 mL/L $H_2O_2$ 1 time per day for 3 d then every other day | 0.0140 mL/L $H_2O_2$ 1 time per day | 0.0140 mL/L $H_2O_2$ 1 time per day for 3 d then every other day | 0.0175 mL/L $H_2O_2$ 1 time per day for 2 d then every other |
| 0 | 0.0 ± 0.0 | 0.0 ± 0.0 | 0.0 ± 0.0 | 0.0 ± 0.0 | 0.0 ± 0.0 | 0.0 ± 0.0 |
| 3 | 0.0 ± 0.0 | 0.0 ± 0.0 | 0.0 ± 0.0 | 0.0 ± 0.0 | 0.0 ± 0.0 | 0.0 ± 0.0 |
| 4 | 14.2 ± 8.3 | 0.8 ± 1.2 | 0.8 ± 1.2 | 0.0 ± 0.0 | 0.0 ± 0.0 | 0.0 ± 0.0 |
| 5 | 21.7 ± 4.7 | 0.8 ± 1.2 | 5.0 ± 2.4 | 0.0 ± 0.0 | 0.0 ± 0.0 | 0.0 ± 0.0 |
| 6 | 36.7 ± 16.5 | 1.7 ± 2.4 | 2.5 ± 1.2 | 0.0 ± 0.0 | 1.7 ± 2.4 | 0.8 ± 1.2 |
| 7 | 17.5 ± 3.5 | 3.3 ± 0.0 | 0.0 ± 0.0 | 1.7 ± 2.4 | 0.0 ± 0.0 | No data |
| 8 | 20.0 ± 7.1 | 0.0 ± 0.0 | 0.0 ± 0.0 | 0.8 ± 1.2 | 0.8 ± 1.2 | No data |
| 9 | 21.7 ± 7.1 | 0.8 ± 1.2 | 2.5 ± 3.5 | 0.8 ± 1.2 | 0.0 ± 0.0 | No data |
| 10 | 26.7 ± 14.1 | 0.0 ± 0.0 | 1.7 ± 2.4 | 0.0 ± 0.0 | 0.0 ± 0.0 | No data |

TABLE 30

| | | Culture Dry Weight (g/L) | | | | |
|---|---|---|---|---|---|---|
| Time (days after inoculation) | Untreated Control | 0.0105 mL/L $H_2O_2$ 1 time per day | 0.0105 mL/L $H_2O_2$ 1 time per day for 3 d then every other day | 0.0140 mL/L $H_2O_2$ 1 time per day | 0.0140 mL/L $H_2O_2$ 1 time per day for 3 d then every other day | 0.0175 mL/L $H_2O_2$ 1 time per day for 2 d then every other day |
| 0 | 0.05 ± 0.01 | 0.05 ± 0.01 | 0.05 ± 0.01 | 0.05 ± 0.01 | 0.05 ± 0.01 | 0.05 ± 0.01 |
| 3 | No data | No data | No data | No data | No data | No data |
| 4 | 0.35 ± 0.03 | 0.32 ± 0.01 | 0.32 ± 0.01 | 0.32 ± 0.01 | 0.32 ± 0.01 | 0.25 ± 0.02 |
| 5 | No data | No data | No data | No data | No data | No data |
| 6 | 0.37 ± 0.02 | 0.35 ± 0.08 | 0.29 ± 0.01 | 0.30 ± 0.03 | 0.35 ± 0.01 | 0.24 ± 0.03 |
| 7 | No Data | No Data | No Data | No Data | No Data | No Data |
| 8 | 0.54 ± 0.06 | 0.42 ± 0.01 | 0.49 ± 0.04 | 0.41 ± 0.05 | 0.48 ± 0.01 | No Data |
| 9 | No Data | No Data | No Data | No Data | No Data | No Data |
| 10 | 0.39 ± 0.04 | 0.38 ± 0.01 | 0.40 ± 0.00 | 0.35 ± 0.04 | 0.38 ± 0.01 | No Data |

As shown in Table 28, percent lysis remained under 10% for control cultures and those treated with 0.0105 mL/L hydrogen peroxide for 11 days. Those treated with 0.0140 mL/L hydrogen peroxide reached 20% lysis by day 7 and those treated with 0.0175 mL/L reached 30% lysis by day 3 after only being dosed twice. These flask cultures were discarded on day 6. Cultures in this set may have been less tolerant to hydrogen peroxide because they were pulled back from the parent reactor within two days of inoculation while in the previous experiment (Example 9), culture samples were pulled back 5 days after inoculation of the parent and were likely further along in cyst stage. As shown in Table 29, chytrid infection reached 20-40% in the untreated controls, but remained less than 10% in all treated flasks. As shown in Table 30, culture dry weights were slightly reduced in flasks treated every day compared to controls and flasks treated every day for 3 days and then every other day. The results show that lower concentrations of hydrogen peroxide are capable of reducing both lysis and chytrid infections, while the high concentrations of hydrogen peroxide were more effective for reducing chytrid infections than lysis.

Example 11

A second flask experiment was conducted to fine tune treatment of 0.03 mL/L 35% stock concentration of hydrogen peroxide (calculated concentration of 0.0105 mL/L) for reducing chytrids in an infected culture of *Haematococcus pluvialis*. Culture samples of *Haematococcus pluvialis* (Strain 2) were collected on the second day of culture from open raceway bioreactor #2410 operating in conditions: reactor volume of 150,000 L; Daily PAR of 9.77 mol m$^{-2}$ d$^{-1}$; pH of 7.3; and paddlewheel speed of 70%. Culture samples were distributed into flasks for culturing, consisting of duplicate untreated controls and duplicate treatments. Treatments compared different frequency doses (once daily, once every other day and once daily for 3 days only) of 0.03 mL/L of 35% stock hydrogen peroxide (calculated concentration of 0.0105 mL/L). Samples were taken from the flask cultures daily to quantify % lysis and % chytrid infection and cell dry weight was quantified every other day for a duration of 11 days. The results are shown in Tables 31-33.

TABLE 31

| | % Lysis | | | |
|---|---|---|---|---|
| Time (days after inoculation) | Untreated Control | 0.0105 mL/L $H_2O_2$ 1 time per day | 0.0105 mL/L $H_2O_2$ 1 time every other day | 0.0105 mL/L $H_2O_2$ 1 time daily for 3 days |
| 1 | 5.0 ± 5.0 | 5.0 ± 5.0 | 5.0 ± 5.0 | 5.0 ± 5.0 |
| 2 | 8.3 ± 0.0 | 2.5 ± 1.2 | 3.3 ± 2.4 | 3.3 ± 0.0 |
| 3 | 3.3 ± 2.4 | 5.8 ± 3.5 | 4.2 ± 1.2 | 7.5 ± 1.2 |
| 4 | 3.3 ± 0.0 | 4.2 ± 1.2 | 3.3 ± 0.0 | 0.8 ± 1.2 |
| 5 | 1.7 ± 2.4 | 4.2 ± 3.5 | 3.3 ± 2.4 | 5.0 ± 0.0 |
| 6 | 0.0 ± 0.0 | 0.0 ± 0.0 | 3.3 ± 2.4 | 4.2 ± 1.2 |
| 7 | 0.0 ± 2.4 | 2.4 ± 0.0 | 3.3 ± 0.0 | 1.7 ± 2.4 |
| 8 | No data | No data | No data | No data |

TABLE 32

| | % Chytrid Infection | | | |
|---|---|---|---|---|
| Time (days after inoculation) | Untreated Control | 0.0105 mL/L $H_2O_2$ 1 time per day | 0.0105 mL/L $H_2O_2$ 1 time every other day | 0.0105 mL/L $H_2O_2$ 1 time daily for 3 days |
| 1 | 0.0 ± 0.0 | 0.0 ± 0.0 | 0.0 ± 0.0 | 0.0 ± 0.0 |
| 2 | 0.0 ± 0.0 | 0.0 ± 0.0 | 0.0 ± 0.0 | 0.0 ± 0.0 |
| 3 | 2.5 ± 3.5 | 0.0 ± 0.0 | 2.5 ± 1.2 | 0.0 ± 0.0 |
| 4 | 1.7 ± 0.0 | 0.0 ± 0.0 | 0.0 ± 0.0 | 0.0 ± 0.0 |
| 5 | 23.3 ± 4.7 | 2.5 ± 3.5 | 0.8 ± 1.2 | 0.8 ± 1.2 |
| 6 | 48.3 ± 4.7 | 0.0 ± 0.0 | 3.3 ± 0.0 | 0.0 ± 0.0 |
| 7 | 92.5 ± 3.5 | 0.0 ± 0.0 | 0.8 ± 1.2 | 1.7 ± 2.4 |
| 8 | No data | No data | No data | No data |

TABLE 33

| | Culture dry weight (g/L) | | | |
|---|---|---|---|---|
| Time (days after inoculation) | Untreated Control | 0.0105 mL/L $H_2O_2$ 1 time per day | 0.0105 mL/L $H_2O_2$ 1 time every other day | 0.0105 mL/L $H_2O_2$ 1 time daily for 3 days |
| 1 | 0.066 ± 0.0 | 0.066 ± 0.0 | 0.066 ± 0.0 | 0.066 ± 0.0 |
| 2 | 0.255 ± 0.021 | 0.210 ± 0.028 | 0.215 ± 0.007 | No data |
| 4 | 0.355 ± 0.049 | 0.308 ± 0.011 | 0.331 ± 0.011 | 0.285 ± 0.0 |
| 6 | 0.500 ± 0.071 | 0.395 ± 0.007 | 0.455 ± 0.021 | 0.475 ± 0.035 |
| 7 | 0.475 ± 0.007 | 0.440 ± 0.028 | 0.540 ± 0.042 | 0.530 ± 0.014 |
| 8 | 0.360 ± 0.057 | 0.490 ± 0.014 | 0.510 ± 0.014 | 0.560 ± 0.028 |

As shown in Table 31, cell lysis remained below 10% in flasks across treatments. As shown in Table 32, chytrid infection remained below 5% in all treated flasks but increased in the untreated control after day 4 to greater than 90% infection. As shown in Table 33, culture dry weight increased in every treatment but noticeably decreased in infected controls after day 6. These results suggest that a conservative treatment of 0.0105 mL/L hydrogen peroxide applied every day, every other day or every day for 3 days only would be sufficient for preventing chytrids in reddening cultures of *Haematococcus pluvialis* while also not affect biomass accumulation.

Example 12

An experiment was conducted to evaluate the effectiveness of salt as a treatment method for reducing chytrids in an infected culture of *Haematococcus pluvialis*, without the addition of hydrogen peroxide. This test was done side by side in flasks (0.1 L) and in reactors located in a greenhouse operating in conditions: reactor volume of 230 L; Daily PAR of 20 mol m$^{-2}$ d$^{-1}$; pH (not measured); and paddlewheel speed of 21 RPM. Flasks were inoculated (100 mL volume) with samples from a culture of green swimmer stage *Haematococcus pluvialis* (Strain 2) cells from open raceway pond outdoor reactor #2410 operating in conditions: reactor volume of 193,750 L; pH of 7.3; and paddlewheel speed of 70%; and brought up to concentration of 2 ppt salt (NaCl). The flask cultures were mixed by shaking at 140 rpm and received 300-400 μmol/m$^2$ s of photosynthetically active radiation (PAR) in 12 hour light cycles and constant supply of 2.5% $CO_2$. The motility of the culture was monitored by visual observation under a microscope. Once the motility of the cells was observed to be below 10%, the level of salt was elevated in duplicate to 4-11 ppt and compared to the culture in two flasks remaining at 2 ppt salt. Nine 230 L reactors were also seeded with culture from bioreactor #2410 on the same day as the flasks and brought to 2 ppt concentration of salt. Once motility of the cells was reduced to <10% (day 3 of culture for flasks and day 2 for 230 L reactors) the level of salt was elevated to a point between 4-18 ppt and compared to the culture in two reactors remaining at 2 ppt salt. Flasks and 230 L reactors were monitored for percentage of cell lysis via visual observation under a microscope, culture dry weight (biomass accumulation in g/L), and percentage of chytrid infection via visual observation under a microscope. Carotenoid production, a proxy for determining astaxanthin, was quantified every other day of culture in the 230 L reactors using the UV method. Results are shown in Tables 34-40.

TABLE 34

% Cell Lysis in Flasks
NaCl concentration (ppt)

| Time (d) | 2 | 4 | 5 | 6 | 7 | 8 | 9 | 10 | 11 |
|---|---|---|---|---|---|---|---|---|---|
| 9 | 0 ± 0% | 0 ± 0% | 0 ± 0% | 4 ± 3% | 0 ± 0% | 3 ± 2% | 0 ± 0% | 1 ± 1% | 0 ± 0% |
| 11 | 0 ± 0% | 0 ± 0% | 1 ± 1% | 5 ± 4% | 7 ± 3% | 2 ± 0% | 2 ± 0% | 3 ± 1% | 1 ± 1% |

TABLE 35

% Cell Lysis in 230 L reactors
NaCl concentration (ppt)

| Time (d) | 2 | 2 | 4 | 5 | 6 | 7 | 8 | 10 | 18 |
|---|---|---|---|---|---|---|---|---|---|
| 2 | 0.00% | 0.00% | 1.67% | 3.18% | 0.00% | 0.00% | 3.18% | 0.00% | 0.00% |
| 3 | 1.67% | 0.00% | 0.00% | 5.00% | 0.00% | 0.00% | 3.33% | 5.00% | 3.33% |
| 4 | 0.00% | 1.67% | 0.00% | 3.33% | 8.33% | 3.33% | 0.00% | 6.67% | 13.33% |
| 5 | 0.00% | 0.00% | 3.33% | 1.67% | 0.00% | 1.67% | 3.33% | 36.67% | 5.00% |
| 6 | 0.00% | 0.00% | 0.00% | 21.67% | 13.33% | 18.33% | 16.67% | 31.67% | 26.67% |
| 7 | 0.00% | 3.33% | 30.00% | 10.00% | 18.33% | 8.33% | 5.00% | 3.33% | 20.00% |
| 8 | 0.00% | 1.67% | 23.33% | 1.67% | 1.67% | 1.67% | 0.00% | 0.00% | 1.67% |
| 9 | 0.00% | 30.00% | 13.33% | 5.00% | 6.67% | 6.67% | 6.67% | 5.00% | 8.33% |
| 10 | 0.00% | 0.00% | 11.67% | 5.00% | 1.67% | 6.67% | 15.00% | 3.33% | 5.00% |
| 11 | 1.67% | no data | 5.00% | 8.33% | 6.67% | 11.67% | 11.67% | 6.67% | 1.67% |
| 12 | 0.00% | no data | 6.67% | 3.33% | 5.00% | 5.00% | 3.33% | 5.00% | 3.33% |

TABLE 36

% Chytrid infection in Flasks
NaCl concentration (ppt)

| Time (d) | 2 | 4 | 5 | 6 | 7 | 8 | 9 | 10 | 11 |
|---|---|---|---|---|---|---|---|---|---|
| 9 | 82 ± 17% | 22 ± 20% | 18 ± 16% | 8 ± 11% | 3 ± 5% | 1 ± 1% | 1 ± 1% | 0 ± 0% | 0 ± 0% |
| 11 | 96 ± 4% | 85 ± 16% | 53 ± 9% | 19 ± 27% | 0 ± 0% | 2 ± 2% | 1 ± 1% | 0 ± 0% | 17 ± 24% |

TABLE 37

% Chytrid infection in 230 L reactors
NaCl concentration (ppt)

| Time (d) | 2 | 2 | 4 | 5 | 6 | 7 | 8 | 10 | 18 |
|---|---|---|---|---|---|---|---|---|---|
| 2 | 1.67% | 0.00% | 0.00% | 1.67% | 1.67% | 3.33% | 0.00% | 0.00% | 0.00% |
| 3 | 0.00% | 0.00% | 1.67% | 0.00% | 0.00% | 0.00% | 0.00% | 0.00% | 0.00% |
| 4 | 0.00% | 0.00% | 0.00% | 1.67% | 1.67% | 0.00% | 0.00% | 1.67% | 0.00% |
| 5 | 0.00% | 0.00% | 0.00% | 0.00% | 1.67% | 1.67% | 0.00% | 0.00% | 3.33% |
| 6 | 0.00% | 0.00% | 0.00% | 0.00% | 1.67% | 0.00% | 0.00% | 0.00% | 0.00% |
| 7 | 8.33% | 3.33% | 1.67% | 8.33% | 5.00% | 5.00% | 0.00% | 0.00% | 0.00% |
| 8 | 16.67% | 21.67% | 0.00% | 0.00% | 3.33% | 1.67% | 0.00% | 0.00% | 1.67% |
| 9 | 45.00% | 10.00% | 11.67% | 10.00% | 0.00% | 3.33% | 0.00% | 1.67% | 3.33% |
| 10 | 71.67% | 100.00% | 30.00% | 3.33% | 1.67% | 5.00% | 1.67% | 0.00% | 0.00% |
| 11 | 81.67% | no data | 36.67% | 13.33% | 0.00% | 0.00% | 1.67% | 6.67% | 1.67% |
| 12 | 100.00% | no data | 65.00% | 28.33% | 15.00% | 3.33% | 3.33% | 3.33% | 1.67% |

TABLE 38

Culture Dry Weight (g/L) in Flasks
NaCl concentration (ppt)

| Time (d) | 2 | 4 | 5 | 6 | 7 | 8 | 9 | 10 | 11 |
|---|---|---|---|---|---|---|---|---|---|
| 0 | 0.044 | 0.044 | 0.044 | 0.044 | 0.044 | 0.044 | 0.044 | 0.044 | 0.044 |
| 11 | 0.49 ± 0.04 | 0.48 ± 0.05 | 0.43 ± 0.04 | 0.48 ± 0.02 | 0.49 ± 0.02 | 0.50 ± 0.04 | 0.45 ± 0.00 | 0.42 ± 0.01 | 0.40 ± 0.04 |

TABLE 39

Culture Dry Weight (g/L) in 230 L reactors
NaCl concentration (ppt)

| Time (d) | 2 | 2 | 4 | 5 | 6 | 7 | 8 | 10 | 18 |
| --- | --- | --- | --- | --- | --- | --- | --- | --- | --- |
| 0 | 0.030 | 0.043 | 0.037 | 0.040 | 0.040 | 0.035 | 0.018 | 0.045 | 0.035 |
| 1 | 0.042 | 0.048 | 0.063 | 0.070 | 0.058 | 0.048 | 0.057 | 0.060 | 0.052 |
| 2 | 0.065 | 0.072 | 0.080 | 0.095 | 0.085 | 0.103 | 0.093 | 0.088 | 0.098 |
| 3 | 0.120 | 0.105 | 0.103 | 0.143 | 0.133 | 0.123 | 0.135 | 0.140 | 0.158 |
| 4 | 0.145 | 0.113 | 0.115 | 0.162 | 0.140 | 0.145 | 0.145 | 0.120 | 0.135 |
| 5 | 0.228 | 0.125 | 0.120 | 0.185 | 0.178 | 0.150 | 0.168 | 0.130 | 0.173 |
| 6 | 0.173 | 0.130 | 0.125 | 0.213 | 0.198 | 0.170 | 0.193 | 0.168 | 0.180 |
| 7 | 0.185 | 0.150 | 0.148 | 0.223 | 0.218 | 0.198 | 0.205 | 0.145 | 0.165 |
| 8 | 0.273 | 0.170 | 0.153 | 0.270 | 0.260 | 0.260 | 0.237 | 0.145 | 0.165 |
| 9 | 0.145 | 0.218 | 0.198 | 0.293 | 0.260 | 0.148 | 0.218 | 0.160 | 0.175 |
| 10 | 0.220 | 0.150 | 0.143 | 0.265 | 0.250 | 0.205 | 0.257 | 0.173 | 0.183 |
| 11 | 0.145 | no data | 0.148 | 0.250 | 0.282 | 0.218 | 0.220 | 0.145 | 0.200 |
| 12 | 0.187 | no data | 0.150 | 0.280 | 0.323 | 0.245 | 0.263 | 0.168 | 0.175 |

TABLE 40

% Carotenoid by UV Method in 230 L reactors
NaCl concentration (ppt)

| Time (d) | 2 | 2 | 4 | 5 | 6 | 7 | 8 | 10 | 18 |
| --- | --- | --- | --- | --- | --- | --- | --- | --- | --- |
| 3 | 1.38 | 1.32 | 1.3 | 1.26 | 1.71 | 1.76 | 1.25 | 1.48 | 1.34 |
| 5 | 2.53 | 2.14 | 2.6 | 3.12 | 2.67 | 2.82 | 2.02 | 1.96 | 1.81 |
| 7 | 3.77 | 3.69 | 3.87 | 5.12 | 4.57 | 4.28 | 4.11 | 2.82 | 2.63 |
| 9 | 3.41 | 3.93 | 3.56 | 5.33 | 4.77 | 4.73 | 4.83 | 3.43 | 2.79 |
| 11 | 3.28 | no data | 5.02 | 5.45 | 5.67 | 5.3 | 5.41 | 6.11 | 4.25 |
| 12 | 3.16 | no data | 3.07 | 5.74 | 5.63 | 5.72 | 5.71 | 4.38 | 3.79 |

As shown in Tables 34 and 35, cell lysis remained below 10% in flasks for all treatments, and below 30% in 230 L reactors across all treatments except 10 ppt. Lysis was highest at 4, 10 and 18 ppt salt. As shown in Table 36 and 37, chytrid infection decreased as salinity increased for both flasks and 230 L reactors. Chytrid infection remained below 5-10% for treatments between 7-10 ppt in flasks, and treatments at 7 ppt and above in 230 L reactors. As shown in Tables 38, the biomass accumulation measured by culture dry weight was similar for all treatments except the two highest salinities, which were reduced. As shown in Table 39, biomass accumulation was highest in the 230 L reactors after day 7 for treatments between 5-8 ppt. As shown in Table 40, carotenoid accumulation was highest for treatments between 5-8 ppt in the 230 L reactors. Visual observation under a microscope showed that cysts in cultures set to 8 ppt were the healthiest and cleanest looking (e.g., large, red, and least fouled) in both flasks and 230 L reactors. These findings suggest that as an alternative to hydrogen peroxide treatments, 8 ppt salt can be used to reduce chytrid infection while maintaining biomass and astaxanthin accumulation.

Example 13

Experiments were performed to determine chytrid tolerance to bleach, salt, Lufenuron (chemical biocide), and Rid Fungus (blend of natural organic herbs) for evaluation as a treatment for chytrids. A pure chytrid culture in a well plate was treated every 24 hours and observed under a microscope to determine the effect. An untreated culture was used as a control for comparison purposes. Qualitative assessments and quantitative estimates were made by visual observation under a microscope.

In the control culture, sporangia and zoospores without tails were observed after 1 hour. Swimming zoospores were observed after 24 hours, sporangia and swimming zoospores (80-100% motility) were observed after 48 hours, and swimming zoospores (90-100%) motility were observed after 72 hours. From the observation of the control culture, a treatment that reduces the formation or motility of zoospores may be further investigated as a viable treatment.

In the culture receiving 0.03 mL/L of bleach 12.5% stock concentration (calculated concentration of 0.00375 mL/L), sporangia and zoospores were observed after 24 hours. Sporangia and swimming zoospores (100% motility) were observed after 48 hours, and swimming zoospores (100% motility) were observed after 72 hours.

In the culture receiving 0.1 mL/L of bleach 12.5% stock concentration (calculated concentration of 0.0125 mL/L), sporangia only was observed after 1 hour. Only bacteria were observed after 24 hours, bacteria and a few zoospores were observed after 48 hours, and bacteria with no zoospores and a few sporangia were observed after 72 hours.

In the culture receiving 0.2 mL/L of bleach 12.5% stock concentration (calculated concentration of 0.025 mL/L), sporangia and zoospores were observed after 1 hour. Swimming zoospores were observed after 24 hours, and bacteria and sporangia only (no zoospores) were observed after 48 hours and 72 hours. The lack of zoospores after 72 hours for the 0.0125 and 0.025 mL/L bleach treatments indicate that the treatment may be effective against chytrids, but the known tolerance of *Haematococcus pluvialis* (Strain 1) is 0.00375 mL/L and thus the higher concentrations would not be viable as a treatment during culturing.

In the culture receiving 20 ppt salt (NaCl), clumped sporangia and zoospores were observed after 1 hour. Wilting sporangia and no zoospores were observed after 24 hours, bacteria with shriveled zoospores and sporangia were observed after 48 hours, and no zoospores or sporangia were observed after 72 hours. The results show that the high level of salt is effective against chytrids, but the level is above the threshold that has been shown to negatively affect some strains of *Haematococcus* during culturing.

In the culture receiving 40 ppm of Lufenuron, swimming zoospores were observed after 1 hour. Swimming zoospores were again observed after 24 hours, and heavy bacteria with sporangia and zoospores were observed after 48 hours and 72 hours. The resulting proliferation of zoospores demonstrates that Lufenuron is not effective as a chytrid treatment.

In the culture receiving 0.01% of Rid Fungus, swimming zoospores were observed after 24 hours. Bacteria only were observed after 48 hours and 72 hours.

In the culture receiving 0.1% of Rid Fungus, sporangia and zoospores were observed after 1 hour. Bacteria and zoospores were observed after 24 hours, bacteria and a few zoospores with no motility were observed after 48 hours, and bacteria only were observed after 72 hours. The results show that Rid Fungus may be effective for treating chytrids, however the effect on *Haematococcus* cells needs to be determined if Rid Fungus is to be used as treatment during culturing.

Example 14

Several concentrations of salt and Rid Fungus (blend of organic herbs) were further investigated as a chytrid treatment, as in Example 13. A pure chytrid culture in a well plate was treated and visually observed under a microscope to determine the effect. An untreated culture was used as a control for comparison purposes.

In the control culture, motile dense zoospores were observed after 1 and 4.5 hours. From the observation of the control culture, a treatment that reduces the formation or motility of zoospores may be further investigated as a viable treatment.

In the culture receiving 5 ppt salt (NaCl), a less dense mass of zoospores with some being motile but sluggish were observed after 1 hour. A mix of non-motile and motile zoospores were observed after 4.5 hours.

In the culture receiving 10 ppt salt (NaCl), a mass of zoospores at the same density as the 5 ppt treatment but with all being non-motile were observed after 1 hour. Non-motile zoospores only were observed after 4.5 hours.

In the culture receiving 20 ppt salt (NaCl), a mass of zoospores less dense than mass of the 5 and 10 ppt treatments but with all being non-motile were observed after 1 hour. Non-motile zoospores only were observed after 4.5 hours. The results show that the high level of salt is effective against chytrids, but the level is above the threshold that has been shown to negatively affect some strains of *Haematococcus* during culturing.

In the culture receiving 0.10% of Rid Fungus, a mass of zoospores less dense than the control but highly motile were observed after 1 hour. Motile zoospores were observed after 4.5 hours.

In the culture receiving 0.25% of Rid Fungus, a mass of zoospores less dense than the control but less motility than the 0.1% treatment were observed after 1 hour. Some motile zoospores and possibly dead sporangia were observed after 4.5 hours.

In the culture receiving 0.50% of Rid Fungus, some motile zoospores were observed after 1 hour. Some motile zoospores and dead sporangia were observed after 4.5 hours. The results show that the higher levels of Rid Fungus may be effective in reducing chytrid zoospores, but the effect on *Haematococcus* cells needs to be determined if Rid Fungus is to be used as treatment during culturing.

Example 15

Several concentrations of bleach and Lufenuron were further investigated for their effectiveness as chytrid treatments for *Haematococcus pluvialis* during culturing. Cultures of *Haematococcus pluvialis* (Strain 1) red cyst cells infected with chytrids were treated in well plates (0.5 mL volume) with bleach or Lufenuron to evaluate the effect on the *Haematococcus* cells if bleach or Lufenuron were to be used as a contamination treatment. A first control culture of *Haematococcus* red cyst cells absent of chytrids and a second control culture of healthy *Haematococcus* red cyst cells inoculated with chytrids were used as comparisons for the treatments. The cultures were treated with bleach at or less than the tolerance level of *Haematococcus*: 0.01, 0.02 and 0.03 mL/L of 12.5% stock concentration bleach (calculated concentration 0.00125, 0.0025, and 0.00375 mL/L), or different concentrations of Lufenuron (0.01, 0.1 and 1% of culture volume). The cultures were observed under a microscope during the experiment to determine effectiveness.

In the first control culture, the cells were observed to be healthy red cysts at the time of inoculation. Healthy red cysts and bacteria were observed after 24 hours. Healthy red cysts and some clumping were observed after 48 hours. Healthy red cysts were observed after 72 hours.

In the second control culture, swimming zoospores and sporangia on red cysts were observed at the time of inoculation. Swimming zoospores and positive infection of the red cyst cells were observed after 24 hours. Bacteria, swimming zoospores, and positive infection of the red cyst cells were observed after 48 hours. Heavy bacteria, few swimming zoospores, and decreased infection of the red cyst cells were observed after 72 hours.

In the culture receiving 0.01 mL/L of bleach 12.5% stock concentration (calculated concentration of 0.00125 mL/L, which is a concentration below the tolerance level of *Haematococcus*), swimming zoospores and positive infection were observed after 24 and 48 hours. Some swimming zoospores, high bacteria, and dead sporangia were observed after 72 hours.

In the culture receiving 0.02 mL/L of bleach 12.5% stock concentration (calculated concentration of 0.0025 mL/L, which is a concentration below the tolerance level of *Haematococcus*), swimming zoospores and positive infection were observed after 24 and 48 hours. Some swimming zoospores and dead sporangia were observed after 72 hours.

In the culture receiving 0.03 mL/L of bleach 12.5% stock concentration (calculated concentration of 0.00375 mL/L, which is a concentration at the tolerance level of *Haematococcus*), swimming zoospores and positive infection were observed after 24. Swimming zoospores, positive infection, and lysed/dead *Haematococcus* cells were observed after 48 hours. Some swimming zoospores, high bacteria, and active infection were observed after 72 hours. Based on the results, the concentrations of bleach below the tolerance level of *Haematococcus* were ineffective at treating chytrids.

In the culture receiving 0.01% of Lufenuron, swimming zoospores and positive infection were observed after 24 and 48 hours. Some swimming zoospores, *Ochromonas* (single-celled, motile, golden-brown alga), and active infection were observed after 72 hours.

In the culture receiving 0.10% of Lufenuron, dead sporangia, some infection, and active zoospores were observed after 24 and 48 hours. Some swimming zoospores and active infection were observed after 72 hours.

In the culture receiving 1.00% of Lufenuron, dead sporangia and zoospores attached to cyst cells were observed after 24 hours. *Ochromonas*, bacteria, dead sporangia, zoospores attached to cyst cells, and few swimming zoospores were observed after 48 hours. *Ochromonas*, no active infection, and no zoospores were observed after 72 hours. Based on the results, concentration of 1% Lufenuron may be an effective treatment for chytrids in a *Haematococcus* culture, however the effect on biomass and carotenoid accumulation needs to be determined.

Example 16

A solution comprising 50% sodium hydroxide (NaOH) was evaluated as a treatment for chytrids that could be applied to empty reactors in order to clean them for subsequent batches. A pure culture of chytrid zoospores and sporangia was treated with a 1% dose of a solution comprising 50% NaOH at temperatures of 25, 40, and 50° C. The cultures were then observed under a microscope for a reduction in the chytrid zoospores or sporangia number, or a reduction in the integrity of the chytrid cells. The results showed that there was not a reduction in chytrid zoospores or sporangia number or integrity for any of the treatments.

Example 17

Experiments were conducted to evaluate the use of biological agents for the control of chytrids in a culture of microalgae. *Ochromonas* is a single-celled, motile, golden-brown alga known to ingest bacteria and small eukaryotes, and was evaluated for its properties as a chytrid zoospore predator. *Janthinobacterium* is a gram-negative soil bacteria known to prey on chytrid zoospores and was evaluated for its properties as such. A pure culture of chytrids was inoculated into well plates. A control was left untreated and compared to cultures treated with *Ochromonas* and *Janthinobacterium*. Chytrid zoospore density was quantified after three days by visual observation under a microscope. Results showed that the culture treated with *Ochromonas* had an average number of zoospores that was approximately half of the culture treated with *Janthinobacterium* and approximately one third of the control. Further testing would have to be performed to determine the effect on *Haematococcus* cells before use as culturing treatment.

ASPECTS OF THE INVENTION

In one non-limiting embodiment of the invention, a method of culturing *Haematococcus pluvialis*, may comprise: culturing a population of *Haematococcus pluvialis* cells in growth conditions in a liquid culture medium to obtain a culture of *Haematococcus pluvialis* cells in which the cells are primarily in a green swimmer stage; contacting the primarily green swimmer stage culture with hydrogen peroxide to form a calculated concentration in the range of 0.005-0.020 mL of hydrogen peroxide per L of culture medium (mL/L); and culturing the *Haematococcus pluvialis* cells in reddening conditions to form cells in the red cyst stage for accumulation of carotenoids.

In some embodiments, the calculated concentration of hydrogen peroxide may be in the range of 0.005-0.010 mL/L. In some embodiments, the calculated concentration of hydrogen peroxide may be in the range of 0.010-0.015 mL/L. In some embodiments, the calculated concentration of hydrogen peroxide is in the range of 0.015-0.020 mL/L.

In some embodiments, the growth conditions may comprise a photosynthetically active radiation intensity in the range of 30-60 mol m$^{-2}$ d$^{-1}$, nitrate concentration in the range of 20-50 ppm in the culture medium, and less than 1 ppt of sodium chloride in the culture medium. In some embodiments, the reddening conditions may comprise the present of 1-5 ppt sodium chloride in the culture medium.

In some embodiments, the method may further comprise determining a level of chytrids in the culture of *Haematococcus pluvialis* cells as a percentage of infected cells out of the total cells in a culture. In some embodiments, the culture of *Haematococcus pluvialis* cells may be contacted with the hydrogen peroxide when the level of chytrids is less than 20%. In some embodiments, the culture of *Haematococcus pluvialis* cells is contacted with the hydrogen peroxide when the level of chytrids is at least 5%.

In some embodiments, the level of chytrids in the culture may be maintained below the level of chytrids at the time of contact with hydrogen peroxide while culturing the *Haematococcus pluvialis* cells in reddening conditions to produce cells in the red cyst stage for the accumulation of carotenoids. In some embodiments, the chytrid level after contacting the culture with hydrogen peroxide may be 20-95% less than a control culture not receiving treatment with hydrogen peroxide.

In some embodiments, the cells may be contacted with the hydrogen peroxide multiple times. In some embodiments, the cells may be contacted with the hydrogen peroxide every 6-24 hours. In some embodiments, the cells may be contacted with the hydrogen peroxide every 6-12 hours. In some embodiments, the cells may be contacted with the hydrogen peroxide every 6-8 hours. In some embodiments, the cells may be contacted with the hydrogen peroxide every day over the course of 1-14 days. In some embodiments, the cells may be contacted with hydrogen peroxide every other day over the course of 3-15 days.

In some embodiments, the biomass yield of the *Haematococcus pluvialis* cells contacted with the hydrogen peroxide may be equivalent to or greater than a control culture not receiving treatment with hydrogen peroxide. In some embodiments, the biomass yield of the *Haematococcus pluvialis* cells contacted with the hydrogen peroxide may be 0.01-0.25 g/L greater than a control culture not receiving treatment with hydrogen peroxide.

In some embodiments, the carotenoids yield of the *Haematococcus pluvialis* cells contacted with the hydrogen peroxide may be equivalent to or greater than a control culture not receiving treatment with hydrogen peroxide. In some embodiments, the carotenoid yield of the *Haematococcus pluvialis* cells contacted with the hydrogen peroxide may be 0.10-1.50% greater than a control culture not receiving treatment with hydrogen peroxide.

In some embodiments, the method may further comprise transferring the culture of *Haematococcus pluvialis* cells to a new culturing vessel after contacting the culture with the hydrogen peroxide.

In one non-limiting embodiment of the invention, a method of culturing *Haematococcus pluvialis* may comprise: culturing a population of *Haematococcus pluvialis* cells in reddening conditions in a liquid culture medium comprising 1-5 ppt of salt to obtain a culture of *Haematococcus pluvialis* cells in which the cells are primarily in a cyst; and contacting the primarily cyst stage culture with hydrogen peroxide to form a calculated concentration in the range of 0.005-0.020 mL of hydrogen peroxide per L of culture medium (mL/L). In some embodiments, the cyst stage may comprise at least one selected from the group consisting of green cysts and red cysts accumulating carotenoids.

In some embodiments, the salt may be sodium chloride. In some embodiments, the sodium chloride may be present in the liquid culture medium at a concentration of 1-3 ppt. In some embodiments, the sodium chloride may be present in the liquid culture medium at a concentration of 1-2 ppt.

In some embodiments, the chytrid level after contacting the culture with the hydrogen peroxide may be 10-95% less than a control culture not receiving treatment with hydrogen peroxide. In some embodiments, the biomass yield of the *Haematococcus pluvialis* cells contacted with the hydrogen peroxide may be 0.01-0.30 g/L greater than a control culture not receiving treatment with hydrogen peroxide.

In one non-limiting embodiment of the invention, a method of culturing *Haematococcus pluvialis* may comprise: culturing a population of *Haematococcus pluvialis* cells in reddening conditions in a liquid culture medium to obtain a culture of *Haematococcus pluvialis* cells in which the cells are primarily in a cyst stage; detecting a presence of chytrids in the culture; and contacting the culture comprising chytrids and red cyst cells with 5-20 ppt salt. In some embodiments, the cyst stage may comprise at least one selected from the group consisting of green cysts and red cysts accumulating carotenoids.

In some embodiments, the salt may be sodium chloride. In some embodiments, the concentration of sodium chloride in the culture medium may be in the range of 5-10 ppt. In some embodiments, the concentration of sodium chloride in the culture medium may be in the range of 10-15 ppt. In some embodiments, the concentration of sodium chloride in the culture medium may be in the range of 15-20 ppt.

In some embodiments, the culture of *Haematococcus pluvialis* cells may be contacted with the salt when a level of cells infected by chytrids is less than 20% of the total cells. In some embodiments, the culture of *Haematococcus pluvialis* cells may be contacted with salt when a level of cells infected by chytrids is at least 5% of the total cells.

In some embodiments, the level of chytrids in the culture may be maintained below the level of chytrids at the time of contact with the salt while culturing the *Haematococcus pluvialis* cells in reddening conditions to form cells in the red cyst stage for the accumulation of carotenoids.

In one non-limiting embodiment of the invention, a method of preventing a chytrid infection in a culture of *Haematococcus pluvialis* may comprise: culturing a population of *Haematococcus pluvialis* cells in a liquid culture medium; determining a number of *Haematococcus pluvialis* cells infected with chytrids in the culture; contacting the culture with hydrogen peroxide when the percentage of *Haematococcus pluvialis* cells infected with chytrids is less than 10% of the total cells; continuing to culture the *Haematococcus pluvialis* cells; and verifying that a percentage of *Haematococcus pluvialis* cells infected with chytrids is less than 10% of the total cells after contact with the hydrogen peroxide.

In one non-limiting embodiment, a method of culturing *Haematococcus pluvialis* may comprise: culturing a population of *Haematococcus pluvialis* cells in a liquid culture medium in growth conditions to obtain a culture of *Haematococcus pluvialis* cells in which the cells are primarily in a green swimmer stage; contacting the primarily green swimmer cell stage culture with hydrogen peroxide to form a calculated concentration in the range of 0.005-0.025 mL of hydrogen peroxide per L of culture medium (mL/L) prior to the formation of cell cysts; and continuing to culture the *Haematococcus pluvialis* cells in growth conditions. In some embodiments, the calculated concentration of hydrogen peroxide may be in the range of 0.005-0.010, 0.010-0.015, 0.015-0.020, or 0.020-0.025

In some embodiments, the method may further comprise determining a level of lysis in the culture of *Haematococcus pluvialis* cells as a percentage of the total *Haematococcus pluvialis* cells in the culture. In some embodiments, the culture of *Haematococcus pluvialis* cells may be contacted with the hydrogen peroxide when the level of lysis is less than 20%. In some embodiments, the culture of *Haematococcus pluvialis* cells may be contacted with the hydrogen peroxide when the level of lysis is less than 5%.

In some embodiments, the level of lysis in the culture may be maintained at or below the level of lysis at the time of contact with the hydrogen peroxide while continuing to culture the *Haematococcus pluvialis* cells in growth conditions. In some embodiments, the lysis level of the *Haematococcus pluvialis* culture after contact with the hydrogen peroxide may be 1-80% less than a lysis level in a control culture not receiving treatment with hydrogen peroxide.

In some embodiments, the method may further comprise determining a live bacteria count in the culture of *Haematococcus pluvialis* cells. In some embodiments, the live bacteria count may be reduced $10\text{-}15\times10^5$ CFU/mL after contact with the hydrogen peroxide. In some embodiments, the live bacteria count may be maintained below $10^7$ CFU/mL following contact with the hydrogen peroxide.

In one non-limiting embodiment, a method of preventing lysis in a culture of *Haematococcus pluvialis* may comprise: culturing a population of *Haematococcus pluvialis* cells in a liquid culture medium in growth conditions to obtain a culture of *Haematococcus pluvialis* cells in which the cells are primarily in a green swimmer stage; determining a level of cell lysis for the *Haematococcus pluvialis* cells; contacting the primarily green swimmer cell stage culture with hydrogen peroxide prior to the formation of cysts when the lysis level of *Haematococcus pluvialis* cells is less than 5%; continuing to culture the *Haematococcus pluvialis* cells in growth conditions; and verifying that the level of lysis of *Haematococcus pluvialis* cells is less than 5% after contact with the hydrogen peroxide.

In one non-limiting embodiments, a microalgae culture composition may comprise: a population of *Haematococcus pluvialis* cells in a liquid culture medium; and a calculated concentration of hydrogen peroxide in the range of 0.005-0.025 mL of hydrogen peroxide per L of culture medium (mL/L), wherein hydrogen peroxide has been added to the culture medium in the previous 120 minutes.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Any claimed embodiment of the invention does not necessarily include all of the "aspects" or "embodiments" of the specification.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

What is claimed is:

1. A method of preventing lysis in a culture of *Haematococcus pluvialis*, comprising:
   a. Culturing a population of *Haematococcus pluvialis* cells in a liquid culture medium in growth conditions to obtain a culture of *Haematococcus pluvialis* cells in which the cells are primarily in a green swimmer stage;
   b. Determining a level of lysis for the *Haematococcus pluvialis* cells as a percentage of cells displaying a loss of cell membrane integrity out of the total *Haematococcus pluvialis* cells in the culture;
   c. Contacting the primarily green swimmer cell stage culture with hydrogen peroxide to form a calculated concentration in the range of 0.005-0.025 mL of hydrogen peroxide per L of culture medium (mL/L) prior to the formation of cysts when the level of lysis of *Haematococcus pluvialis* cells is less than 5%;
   d. Continuing to culture the *Haematococcus pluvialis* cells in growth conditions; and
   e. Verifying that the level of lysis of *Haematococcus pluvialis* cells is maintained at a level less than 5% after contact with the hydrogen peroxide.

2. The method of claim 1, wherein the calculated concentration of hydrogen peroxide is in the range of 0.005-0.010 mL/L.

3. The method of claim 1, wherein the calculated concentration of hydrogen peroxide is in the range of 0.010-0.015 mL/L.

4. The method of claim 1, wherein the calculated concentration of hydrogen peroxide is in the range of 0.015-0.020 mL/L.

5. The method of claim 1, wherein the calculated concentration of hydrogen peroxide is in the range of 0.020-0.025 mL/L.

6. The method of claim 1, wherein the growth conditions comprise a photosynthetically active radiation intensity below 30-60 mol $m^{-2}$ $d^{-1}$, nitrates in the range of 20-50 ppm in the culture medium, and less than 1 ppt of sodium chloride in the culture medium.

7. The method of claim 1, wherein the cells are contacted with the hydrogen peroxide multiple times.

8. The method of claim 7, wherein the cells are contacted with the hydrogen 2-4 times per day.

9. The method of claim 7, wherein the cells are contacted with the hydrogen peroxide every day over the course of 1-14 days.

10. The method of claim 7, wherein the cells are contacted with the hydrogen peroxide every other day for a period of 3-15 days.

11. The method of claim 1, wherein the biomass yield of the *Haematococcus pluvialis* cells contacted with hydrogen peroxide is equivalent to or greater than a control culture not receiving treatment with hydrogen peroxide.

12. The method of claim 11, wherein the biomass yield of the *Haematococcus pluvialis* cells contacted with hydrogen peroxide is 0.01-0.25 g/L greater than a control culture not receiving treatment with hydrogen peroxide.

13. The method of claim 1, wherein the method further comprises:
   a. Determining a live bacteria count in the culture of *Haematococcus pluvialis* cells.

14. The method of claim 13, wherein the live bacteria count is reduced $10\text{-}15 \times 10^5$ CFU/mL after contact with the hydrogen peroxide.

15. The method of claim 13, wherein the live bacteria count is maintained below $10^7$ CFU/mL following contact with the hydrogen peroxide.

* * * * *